United States Patent
Ashton et al.

[11] Patent Number: 5,854,420
[45] Date of Patent: Dec. 29, 1998

[54] MAIZE ACETYL COA CARBOXYLASE ENCODING DNA CLONES

[75] Inventors: Anthony Richard Ashton, Cook; Colin Leslie Dow Jenkins, Evatt; Paul Raymond Whitfeld, Hackett, all of Australia

[73] Assignees: Zeneca Limited, United Kingdom; ICI Australia Operations Proprietary Limited, Australia

[21] Appl. No.: 244,537

[22] PCT Filed: Nov. 27, 1992

[86] PCT No.: PCT/GB92/02205

§ 371 Date: Aug. 18, 1994

§ 102(e) Date: Aug. 18, 1994

[87] PCT Pub. No.: WO93/11243

PCT Pub. Date: Jun. 10, 1993

[30] Foreign Application Priority Data

Nov. 28, 1991 [GB] United Kingdom ............ 9125330

[51] Int. Cl.⁶ ............... A01H 5/00; C12N 15/29; C12N 15/82
[52] U.S. Cl. ............ 800/205; 536/23.2; 536/23.6; 435/69.1; 435/134; 435/172.3; 435/320.1; 800/DIG. 56
[58] Field of Search ............ 536/23.6, 23.2, 536/24.1, 24.5; 435/69.1, 70.1, 172.3, 134, 320.1; 800/205, DIG. 56, DIG. 52

[56] References Cited

U.S. PATENT DOCUMENTS 5,290,696  3/1994  Somers et al. ............ 435/240.5

FOREIGN PATENT DOCUMENTS 255378  2/1988  European Pat. Off. .
469810  2/1992  European Pat. Off. .
9110725  7/1991  WIPO .

OTHER PUBLICATIONS

Nikolau et al. 1984. Plant Physiol. 75:895–901.
Broglie et al. 1981. Proc. Natl. Acad. Sci. USA 78(12):7304–7308.
Nikolau et al. 1991. Int. Soc. Plant Mol. Biol., 3rd Int. Cong., Oct. 6–10, 1991, poster #720.
Nikolau et al. 1984. Archives Biochem. Biophys. 235(2):555–561.
Rogers et al. 1983. J. Biol. Chem. 258(13):8169–8174.
Lopez–Casillas et al. 1988. Proc. Natl. Acad. Sci. USA 85:5784–5788.
Livne et al. 1990. Plant Cell Physiol. 31(6):851–858.
Napoli et al. 1990. Plant Cell 2:279–289.
Smith et al. 1988. Nature 334:724–726
Sheehy et al. 1988. Proc. Natl. Acad. Sci. USA 85:8805–8809.
Chang et al. 1985. Mol. Cell. Biol. 5(9):2341–2348.
Kim et al. 1994. Plant Mol. Biol. 24:105–117.
Lewin, R. 1987. Science 237:1570
Reeck et al. 1987. Cell 5D:667
Slabas et al: "The biochemistry and molecular biology of plant lipid biosyntheses", Plant Molecular Biology vol. 19, 1992, pp. 169–191, & Nikolau et al: Molecular cloning and characterization of acetyl–CoA carboxylase and other biotin enzymes of plants, International Society of Plant Molecular Biology, 3rd International Congress Oct. 1991, Poster 720.
Egli et al: "Purification and characterization of maize acetyl–CoA carboxylase", Plant Physiology, vol. 96, No. 1, May 1991, page 92–see abstract 581.
Parker et al: "Dominant mutations causing alterations in acetyl–coenzyme A carboxylase confer tolerance to cyclohexanedione and aryloxyphenoxypropionate herbicides in maize", Proceedings of the National Academy of Sciences of USE, vol. 87. Sep. 1990, pp. 7175–7179, see the whole document.

*Primary Examiner*—David T. Fox
*Attorney, Agent, or Firm*—Cushman Darby & Cushman; IP Group of Pillsbury; Madison & Sutro LLP

[57] ABSTRACT

Clones are disclosed comprising at least part of a DNA sequence of a gene encoding maize acetyl CoA carboxylase, or a sequence showing substantial homology therewith, flanked by heterologous DNA. DNA from such clones may be used to isolate similar sequences in other plants. Such sequences may be used to transform plants to give a variety of useful effects, including resistance to herbicides such as fluazifop, and modified oil-bearing properties.

6 Claims, 16 Drawing Sheets

FIG. 3(a)

```
     GTTTTTTTTTTTTATTTCATGGCAGTCTGACGTGATTGAAACATTGCGG
  1  ---------+---------+---------+---------+---------+   50
     CAAAAAAAAAAAAATAAAGTACCGTCAGACTGCACTAACTTTGTAACGCC
      F   F   F   F   I   S   W   Q   S   D   V   I   E   T   L   R

CATCAGCACAGTAAAGACCTGCAGAAGGTTGTAGACATTGTGTTGTCTCA
 51  ---------+---------+---------+---------+---------+  100
     GTAGTCGTGTCATTTCTGGACGTCTTCCAACATCTGTAACACAACAGAGT
      H   Q   H   S   K   D   L   Q   K   V   V   D   I   V   L   S   H

CCAGGGTGTGAGGAACAAAGCTAAGCTTGTAACGGCACTTATGGAAAAGC
101  ---------+---------+---------+---------+---------+  150
     GGTCCCACACTCCTTGTTTCGATTCGAACATTGCCGTGAATACCTTTTCG
      Q   G   V   R   N   K   A   K   L   V   T   A   L   M   E   K   L

TGGTTTATCCAAATCCTGGTGGTTACAGGGATCTGTTAGTTCGCTTTTCT
151  ---------+---------+---------+---------+---------+  200
     ACCAAATAGGTTTAGGACCACCAATGTCCCTAGACAATCAAGCGAAAAGA
      V   Y   P   N   P   G   G   Y   R   D   L   L   V   R   F   S

TCCCTCAATCATAAAAGATATTATAAGTTGGCCCTTAAAGCAAGTGAACT
201  ---------+---------+---------+---------+---------+  250
     AGGGAGTTAGTATTTTCTATAATATTCAACCGGGAATTTCGTTCACTTGA
      S   L   N   H   K   R   Y   Y   K   L   A   L   K   A   S   E   L

TCTTGAACAAACCAAACTAAGTGAACTCCGTGCAAGCGTTGCAAGAAGCC
251  ---------+---------+---------+---------+---------+  300
     AGAACTTGTTTGGTTTGATTCACTTGAGGCACGTTCGCAACGTTCTTCGG
      L   E   Q   T   K   L   S   E   L   R   A   S   V   A   R   S   L

TTTCGGATCTGGGGATGCATAAGGGAGAAATGAGTATTAAGGATAACATG
301  ---------+---------+---------+---------+---------+  350
     AAAGCCTAGACCCCTACGTATTCCCTCTTTACTCATAATTCCTATTGTAC
      S   D   L   G   M   H   K   G   E   M   S   I   K   D   N   M

GAAGATTTAGTCTCTGCCCCATTACCTGTTGAAGATGCTCTGATTTCTTT
351  ---------+---------+---------+---------+---------+  400
     CTTCTAAATCAGAGACGGGGTAATGGACAACTTCTACGAGACTAAAGAAA
      E   D   L   V   S   A   P   L   P   V   E   D   A   L   I   S   L
```

FIG. 3(b)

```
         GTTTGATTACAGTGATCGAACTGTTCAGCAGAAAGTGATTGAGACATACA
401      ----------+----------+----------+----------+----------+   450
         CAAACTAATGTCACTAGCTTGACAAGTCGTCTTTCACTAACTCTGTATGT
          F  D  Y  S  D  R  T  V  Q  Q  K  V  I  E  T  Y  I

TATCACGATTGTACCAGCCTCATCTTGTAAAGGATAGCATCCAAATGAAA
451      ----------+----------+----------+----------+----------+   500
         ATAGTGCTAACATGGTCGGAGTAGAACATTTCCTATCGTAGGTTTACTTT
           S  R  L  Y  Q  P  H  L  V  K  D  S  I  Q  M  K

TTCAAGGAATCTGGTGCTATTACTTTTTGGGAATTTTATGAAGGGCATGT
501      ----------+----------+----------+----------+----------+   550
         AAGTTCCTTAGACCACGATAATGAAAACCCTTAAAATACTTCCCGTACA
          F  K  E  S  G  A  I  T  F  W  E  F  Y  E  G  H  V

TGATACTAGAAATGGACATGGGGCTATTATTGGTGGGAAGCGATGGGGTG
551      ----------+----------+----------+----------+----------+   600
         ACTATGATCTTTACCTGTACCCCGATAATAACCACCCTTCGCTACCCCAC
          D  T  R  N  G  H  G  A  I  I  G  G  K  R  W  G  A

CCATGGTCGTTCTCAAATCACTTGAATCTGCGTCAACAGCCATTGTGGCT
601      ----------+----------+----------+----------+----------+   650
         GGTACCAGCAAGAGTTTAGTGAACTTAGACGCAGTTGTCGGTAACACCGA
            M  V  V  L  K  S  L  E  S  A  S  T  A  I  V  A

GCATTAAAGGATTCGGCACAGTTCAACAGCTCTGAGGGCAACATGATGCA
651      ----------+----------+----------+----------+----------+   700
         CGTAATTTCCTAAGCCGTGTCAAGTTGTCGAGACTCCCGTTGTACTACGT
          A  L  K  D  S  A  Q  F  N  S  S  E  G  N  M  M  H

CATTGCATTATTGAGTGCTGAAAATGAAAGTAATATAAGTGGAATAAGTG
701      ----------+----------+----------+----------+----------+   750
         GTAACGTAATAACTCACGACTTTTACTTTCATTATATTCACCTTATTCAC
            I  A  L  L  S  A  E  N  E  S  N  I  S  G  I  S  D

ATGATCAAGCTCAACATAAGATGGAAAAGCTTAGCAAGATACTGAAGGAT
751      ----------+----------+----------+----------+----------+   800
         TACTAGTTCGAGTTGTATTCTACCTTTTCGAATCGTTCTATGACTTCCTA
           D  Q  A  Q  H  K  M  E  K  L  S  K  I  L  K  D

ACTAGCGTTGCAAGTGATCTCCAAGCTGCTGGTTTGAAGGTTATAAGTTG
801      ----------+----------+----------+----------+----------+   850
         TGATCGCAACGTTCACTAGAGGTTCGACGACCAAACTTCCAATATTCAAC
           T  S  V  A  S  D  L  Q  A  A  G  L  K  V  I  S  C
```

FIG. 3(c)

```
     CATTGTTCAAAGAGATGAAGCTCGCATGCCAATGCGCCACACATTCCTCT
851  ----------+----------+----------+----------+----------+  900
     GTAACAAGTTTCTCTACTTCGAGCGTACGGTTACGCGGTGTGTAAGGAGA
      I  V  Q  R  D  E  A  R  M  P  M  R  H  T  F  L  W

GGTTGGATGACAAGAGTTGTTATGAAGAAGAGCAGATTCTCCGGCATGTG
901  ----------+----------+----------+----------+----------+  950
     CCAACCTACTGTTCTCAACAATACTTCTTCTCGTCTAAGAGGCCGTACAC
       L  D  D  K  S  C  Y  E  E  E  Q  I  L  R  H  V

GAGCCTCCCCTCTCTACACTTCTTGAATTGGATAAGTTGAAGGTGAAAGG
951  ----------+----------+----------+----------+----------+  1000
     CTCGGAGGGGAGAGATGTGAAGAACTTAACCTATTCAACTTCCACTTTCC
      E  P  P  L  S  T  L  L  E  L  D  K  L  K  V  K  G

ATACAATGAAATGAAGTATACTCCTTCGCGTGACCGCCAATGGCATATCT
1001 ----------+----------+----------+----------+----------+  1050
     TATGTTACTTTACTTCATATGAGGAAGCGCACTGGCGGTTACCGTATAGA
       Y  N  E  M  K  Y  T  P  S  R  D  R  Q  W  H  I  Y

ACACACTAAGAAATACTGAAAACCCCAAAATGTTGCATAGGGTGTTTTTC
1051 ----------+----------+----------+----------+----------+  1100
     TGTGTGATTCTTTATGACTTTTGGGGTTTTACAACGTATCCCACAAAAAG
        T  L  R  N  T  E  N  P  K  M  L  H  R  V  F  F

CGAACTATTGTCAGGCAACCCAATGCAGGCAACAAGTTTACATCGGCTCA
1101 ----------+----------+----------+----------+----------+  1150
     GCTTGATAACAGTCCGTTGGGTTACGTCCGTTGTTCAAATGTAGCCGAGT
      R  T  I  V  R  Q  P  N  A  G  N  K  F  T  S  A  Q

GATCAGCGACGCTGAAGTAGGATGTCCCGAAGAATCTCTTTCATTTACAT
1151 ----------+----------+----------+----------+----------+  1200
     CTAGTCGCTGCGACTTCATCCTACAGGGCTTCTTAGAGAAAGTAAATGTA
       I  S  D  A  E  V  G  C  P  E  E  S  L  S  F  T  S

CAAATAGCATCTTAAGATCATTGATGACTGCTATTGAAGAATTAGAGCTT
1201 ----------+----------+----------+----------+----------+  1250
     GTTTATCGTAGAATTCTAGTAACTACTGACGATAACTTCTTAATCTCGAA
       N  S  I  L  R  S  L  M  T  A  I  E  E  L  E  L

CATGCAATTAGGACAGGTCATTCTCACATGTATTTGTGCATACTGAAAGA
1251 ----------+----------+----------+----------+----------+  1300
     GTACGTTAATCCTGTCCAGTAAGAGTGTACATAAACACGTATGACTTTCT
       H  A  I  R  T  G  H  S  H  M  Y  L  C  I  L  K  E
```

FIG. 3(d)

```
      GCAAAAGCTTCTTGACCTCATTCCATTTTCAGGGAGTACAATTGTTGATG
1301  ---------+---------+---------+---------+---------+  1350
      CGTTTTCGAAGAACTGGAGTAAGGTAAAAGTCCCTCATGTTAACAACTAC
       Q  K  L  L  D  L  I  P  F  S  G  S  T  I  V  D  V

TTGGCCAAGATGAAGCTACCGCTTGTTCACTTTTAAAATCAATGGCTTTG
1351  ---------+---------+---------+---------+---------+  1400
      AACCGGTTCTACTTCGATGGCGAACAAGTGAAAATTTTAGTTACCGAAAC
        G  Q  D  E  A  T  A  C  S  L  L  K  S  M  A  L

AAGATACATGAGCTTGTTGGTGCAAGGATGCATCATCTGTCTGTATGCCA
1401  ---------+---------+---------+---------+---------+  1450
      TTCTATGTACTCGAACAACCACGTTCCTACGTAGTAGACAGACATACGGT
        K  I  H  E  L  V  G  A  R  M  H  H  L  S  V  C  Q

GTGGGAGGTGAAACTCAAGTTGGACTGTGATGGCCCTGCAAGTGGTACCT
1451  ---------+---------+---------+---------+---------+  1500
      CACCCTCCACTTTGAGTTCAACCTGACACTACCGGGACGTTCACCATGGA
        W  E  V  K  L  K  L  D  C  D  G  P  A  S  G  T  W

GGAGAGTTGTAACTACAAATGTTACTGGTCACACCTGCACCATTGATATA
1501  ---------+---------+---------+---------+---------+  1550
      CCTCTCAACATTGATGTTTACAATGACCAGTGTGGACGTGGTAACTATAT
         R  V  V  T  T  N  V  T  G  H  T  C  T  I  D  I

TACCGAGAAGTGGAGGAAATAGAATCGCAGAAGTTAGTGGTACCATTCAG
1551  ---------+---------+---------+---------+---------+  1600
      ATGGCTCTTCACCTCCTTTATCTTAGCGTCTTCAATCACCATGGTAAGTC
        Y  R  E  V  E  E  I  E  S  Q  K  L  V  V  P  F  S

CCACTTCGTCAGCTGGACCATTGCATGGTGTGCACTGAATAATCCATATC
1601  ---------+---------+---------+---------+---------+  1650
      GGTGAAGCAGTCGACCTGGTAACGTACCACACGTGACTTATTAGGTATAG
         H  F  V  S  W  T  I  A  W  C  A  L  N  N  P  Y  Q

AACCTTTGAGTGTGATTGATCTAAAGCGCTGCTCTGCTAGGAACAACAGA
1651  ---------+---------+---------+---------+---------+  1700
      TTGGAAACTCACACTAACTAGATTTCGCGACGAGACGATCCTTGTTGTCT
          P  L  S  V  I  D  L  K  R  C  S  A  R  N  N  R

ACAACATATTGCTATGATTTTCCGCTGGCCTTTGAAACTGCACTGCAGAA
1701  ---------+---------+---------+---------+---------+  1750
      TGTTGTATAACGATACTAAAAGGCGACCGGAAACTTTGACGTGACGTCTT
         T  T  Y  C  Y  D  F  P  L  A  F  E  T  A  L  Q  K
```

FIG. 3(e)

```
     GTCATGGCAGTCCAATGGCTCTACTGTTTCTGAAGGCAATGAAAATAGTA
1751 ----------+---------+---------+---------+---------+ 1800
     CAGTACCGTCAGGTTACCGAGATGACAAAGACTTCCGTTACTTTTATCAT
      S  W  Q  S  N  G  S  T  V  S  E  G  N  E  N  S  K

AATCCTACGTGAAGGCAACTGAGCTAGTGTTTGCTGAAAAACATGGGTCC
1801 ----------+---------+---------+---------+---------+ 1850
     TTAGGATGCACTTCCGTTGACTCGATCACAAACGACTTTTTGTACCCAGG
       S  Y  V  K  A  T  E  L  V  F  A  E  K  H  G  S

TGGGGCACTCCTATAATTCCGATGGANACCGCTGCTGGGCTCAACGACAT
1851 ----------+---------+---------+---------+---------+ 1900
     ACCCCGTGAGGATATTAAGGCTACCTNTGGCGACGACCCGAGTTGCTGTA
      W  G  T  P  I  I  P  M  X  T  A  A  G  L  N  D  I

TGGTATGGTCGCTTGGATCATGGAGATGTCAACACCTGAATTTCCCAATG
1901 ----------+---------+---------+---------+---------+ 1950
     ACCATACCAGCGAACCTAGTACCTCTACAGTTGTGGACTTAAAGGGTTAC
        G  M  V  A  W  I  M  E  M  S  T  P  E  F  P  N  G

GCAGGCAGATTATTGTTGTAGCAAATGATATCACTTTCAGAGCTGGATCA
1951 ----------+---------+---------+---------+---------+ 2000
     CGTCCGTCTAATAACAACATCGTTTACTATAGTGAAAGTCTCGACCTAGT
        R  Q  I  I  V  V  A  N  D  I  T  F  R  A  G  S

TTTGGCCCAAGGGAAGATGCATTTTTTGAAACTGTCACTAACCTGGCTTG
2001 ----------+---------+---------+---------+---------+ 2050
     AAACCGGGTTCCCTTCTACGTAAAAAACTTTGACAGTGATTGGACCGAAC
      F  G  P  R  E  D  A  F  F  E  T  V  T  N  L  A  C

CGAAAGGAAACTTCCTCTTATATACTTGGCAGCAAACTCTGGTTCTAGGA
2051 ----------+---------+---------+---------+---------+ 2100
     GCTTTCCTTTGAAGGAGAATATATGAACCGTCGTTTGAGACCAAGATCCT
        E  R  K  L  P  L  I  Y  L  A  A  N  S  G  S  R  I

TTGGCATAGCTGATGAAGTAAAATCTTGCTTCCGTGTTGGATGGTCTGAC
2101 ----------+---------+---------+---------+---------+ 2150
     AACCGTATCGACTACTTCATTTTAGAACGAAGGCACAACCTACCAGACTG
         G  I  A  D  E  V  K  S  C  F  R  V  G  W  S  D

GAAGGCAGTCCTGAACGAGGGTTTCAGTACATCTATCTGACTGAAGAAGA
2151 ----------+---------+---------+---------+---------+ 2200
     CTTCCGTCAGGACTTGCTCCCAAAGTCATGTAGATAGACTGACTTCTTCT
       E  G  S  P  E  R  G  F  Q  Y  I  Y  L  T  E  E  D
```

FIG. 3(f)

```
     CTATGCTCGCATTAGCTCTTCTGTTATAGCACATAAGCTGGAGCTAGATA
2201 ----------+---------+---------+---------+---------+ 2250
     GATACGAGCGTAATCGAGAAGACAATATCGTGTATTCGACCTCGATCTAT
      Y  A  R  I  S  S  S  V  I  A  H  K  L  E  L  D  S

GTGGTGAAATTAGGTGGATTATTGACTCTGTTGTGGGCAAGGAGGATGGG
2251 ----------+---------+---------+---------+---------+ 2300
     CACCACTTTAATCCACCTAATAACTGAGACAACACCCGTTCCTCCTACCC
       G  E  I  R  W  I  I  D  S  V  V  G  K  E  D  G

CTTGGTGTCGAGAACATACATGGAAGTGCTGCTATTGCCAGTGCTTATTC
2301 ----------+---------+---------+---------+---------+ 2350
     GAACCACAGCTCTTGTATGTACCTTCACGACGATAACGGTCACGAATAAG
      L  G  V  E  N  I  H  G  S  A  A  I  A  S  A  Y  S

TAGGGCATATGAGGAGACATTTACACTTACATTTGTGACTGGGCGGACTG
2351 ----------+---------+---------+---------+---------+ 2400
     ATCCCGTATACTCCTCTGTAAATGTGAATGTAAACACTGACCCGCCTGAC
        R  A  Y  E  E  T  F  T  L  T  F  V  T  G  R  T  V

TAGGAATAGGAGCTTATCTTGCTCGACTTGGTATACGGTGCATACAGCGT
2401 ----------+---------+---------+---------+---------+ 2450
     ATCCTTATCCTCGAATAGAACGAGCTGAACCATATGCCACGTATGTCGCA
        G  I  G  A  Y  L  A  R  L  G  I  R  C  I  Q  R

CTTGACCAGCCTATTATTTTAACAGGGTTTTCTGCCCTGAACAAGCTCCT
2451 ----------+---------+---------+---------+---------+ 2500
     GAACTGGTCGGATAATAAAATTGTCCCAAAAGACGGGACTTGTTCGAGGA
      L  D  Q  P  I  I  L  T  G  F  S  A  L  N  K  L  L

TGGGCGGGAAGTGTACAGCTCCCACATGCAGCTTGGTGGTCCTAAGATCA
2501 ----------+---------+---------+---------+---------+ 2550
     ACCCGCCCTTCACATGTCGAGGGTGTACGTCGAACCACCAGGATTCTAGT
       G  R  E  V  Y  S  S  H  M  Q  L  G  G  P  K  I  M

TGGCGACCAATGGTGTTGTCCACCTCACTGTTCCAGATGACCTTGAAGGT
2551 ----------+---------+---------+---------+---------+ 2600
     ACCGCTGGTTACCACAACAGGTGGAGTGACAAGGTCTACTGGAACTTCCA
         A  T  N  G  V  V  H  L  T  V  P  D  D  L  E  G

GTTTCCAATATATTGAGGTGGCTCAGCTATGTTCCTGCAAACATTGGTGG
2601 ----------+---------+---------+---------+---------+ 2650
     CAAAGGTTATATAACTCCACCGAGTCGATACAAGGACGTTTGTAACCACC
        V  S  N  I  L  R  W  L  S  Y  V  P  A  N  I  G  G
```

FIG. 3(g)

```
      ACCTCTTCCTATTACCAAACCTCTGGACCCTCCAGACAGACCTGTTGCTT
2651  ----------+----------+----------+----------+----------+  2700
      TGGAGAAGGATAATGGTTTGGAGACCTGGGAGGTCTGTCTGGACAACGAA
       P  L  P  I  T  K  P  L  D  P  P  D  R  P  V  A  Y

ACATCCCTGAGAACACATGCGATCCACGTGCAGCTATCTGTGGTGTAGAT
2701  ----------+----------+----------+----------+----------+  2750
      TGTAGGGACTCTTGTGTACGCTAGGTGCACGTCGATAGACACCACATCTA
        I  P  E  N  T  C  D  P  R  A  A  I  C  G  V  D

GACAGCCAAGGGAAATGGTTGGGTGGTATGTTTGACAAAGACAGCTTTGT
2751  ----------+----------+----------+----------+----------+  2800
      CTGTCGGTTCCCTTTACCAACCCACCATACAAACTGTTTCTGTCGAAACA
       D  S  Q  G  K  W  L  G  G  M  F  D  K  D  S  F  V

GGAGACATTTGAAGGATGGGCAAAAACAGTGGTTACTGGCAGAGCAAAGC
2801  ----------+----------+----------+----------+----------+  2850
      CCTCTGTAAACTTCCTACCCGTTTTTGTCACCAATGACCGTCTCGTTTCG
       E  T  F  E  G  W  A  K  T  V  V  T  G  R  A  K  L

TTGGAGGAATTCCTGTGGGCGTCATAGCTGTGGAGACACAGACCATGATG
2851  ----------+----------+----------+----------+----------+  2900
      AACCTCCTTAAGGACACCCGCAGTATCGACACCTCTGTGTCTGGTACTAC
        G  G  I  P  V  G  V  I  A  V  E  T  Q  T  M  M

CAGATCATCCCTGCTGATCCAGGTCAGCTTGATTCCCATGAGCGATCTGT
2901  ----------+----------+----------+----------+----------+  2950
      GTCTAGTAGGGACGACTAGGTCCAGTCGAACTAAGGGTACTCGCTAGACA
       Q  I  I  P  A  D  P  G  Q  L  D  S  H  E  R  S  V

CCCTCGTGCTGGACAAGTGTGGTTCCCAGATTCTGCAACCAAGACCGCTC
2951  ----------+----------+----------+----------+----------+  3000
      GGGAGCACGACCTGTTCACACCAAGGGTCTAAGACGTTGGTTCTGGCGAG
        P  R  A  G  Q  V  W  F  P  D  S  A  T  K  T  A  Q

AGGCATTATTAGACTTCAACCGTGAAGGATTGCCTCTGTTCATCCTGGCT
3001  ----------+----------+----------+----------+----------+  3050
      TCCGTAATAATCTGAAGTTGGCACTTCCTAACGGAGACAAGTAGGACCGA
        A  L  L  D  F  N  R  E  G  L  P  L  F  I  L  A

AATTGGAGAGGCTTCTCTGGTGGACAAAGAGATCTCTTTGAAGGAATTCT
3051  ----------+----------+----------+----------+----------+  3100
      TTAACCTCTCCGAAGAGACCACCTGTTTCTCTAGAGAAACTTCCTTAAGA
       N  W  R  G  F  S  G  G  Q  R  D  L  F  E  G  I  L
```

FIG. 3(h)

```
       TCAGGCTGGGTCAACAATTGTCGAGAACCTTAGGACATATAATCAGCCTG
3101   --------+---------+---------+---------+---------+   3150
       AGTCCGACCCAGTTGTTAACAGCTCTTGGAATCCTGTATATTAGTCGGAC
        Q  A  G  S  T  I  V  E  N  L  R  T  Y  N  Q  P  A

CTTTTGTGTACATTCCTATGGCTGGAGAGCTTCGTGGAGGAGCTTGGGTT
3151   --------+---------+---------+---------+---------+   3200
       GAAAACACATGTAAGGATACCGACCTCTCGAAGCACCTCCTCGAACCCAA
         F  V  Y  I  P  M  A  G  E  L  R  G  G  A  W  V

GTGGTCGATAGCAAAATAAATCCAGACCGCATTGAGTGTTATGCTGAAAG
3201   --------+---------+---------+---------+---------+   3250
       CACCAGCTATCGTTTTATTTAGGTCTGGCGTAACTCACAATACGACTTTC
        V  V  D  S  K  I  N  P  D  R  I  E  C  Y  A  E  R

GACTGCCAAAGGTAATGTTCTCGAACCTCAAGGGTTAATTGAAATCAAGT
3251   --------+---------+---------+---------+---------+   3300
       CTGACGGTTTCCATTACAAGAGCTTGGAGTTCCCAATTAACTTTAGTTCA
        T  A  K  G  N  V  L  E  P  Q  G  L  I  E  I  K  F

TCAGGTCAGAGGAACTCCAAGACTGTATGGGTAGGCTTGACCCAGAGTTG
3301   --------+---------+---------+---------+---------+   3350
       AGTCCAGTCTCCTTGAGGTTCTGACATACCCATCCGAACTGGGTCTCAAC
        R  S  E  E  L  Q  D  C  M  G  R  L  D  P  E  L

ATAAATCTGAAAGCAAAACTCCAAGATGTAAATCATGGAAATGGAAGTCT
3351   --------+---------+---------+---------+---------+   3400
       TATTTAGACTTTCGTTTTGAGGTTCTACATTTAGTACCTTTACCTTCAGA
        I  N  L  K  A  K  L  Q  D  V  N  H  G  N  G  S  L

ACCAGACATAGAAGGGATTCGGAAGAGTATAGAAGCACGTACGAAACAGT
3401   --------+---------+---------+---------+---------+   3450
       TGGTCTGTATCTTCCCTAAGCCTTCTCATATCTTCGTGCATGCTTTGTCA
         P  D  I  E  G  I  R  K  S  I  E  A  R  T  K  Q  L

TGCTGCCTTTATATACCCAGATTGCAATACGGTTTGCTGAATTGCATGAT
3451   --------+---------+---------+---------+---------+   3500
       ACGACGGAAATATATGGGTCTAACGTTATGCCAAACGACTTAACGTACTA
          L  P  L  Y  T  Q  I  A  I  R  F  A  E  L  H  D

ACTTCCCTAAGAATGGCAGCTAAAGGTGTGATTAAGAAAGTTGTAGACTG
3501   --------+---------+---------+---------+---------+   3550
       TGAAGGGATTCTTACCGTCGATTTCCACACTAATTCTTTCAACATCTGAC
        T  S  L  R  M  A  A  K  G  V  I  K  K  V  V  D  W
```

FIG. 3(i)

```
      GGAAGAATCACGCTCGTTCTTCTATAAAAGGCTACGGAGGAGGATCGCAG
3551  --------+---------+---------+---------+---------+  3600
      CCTTCTTAGTGCGAGCAAGAAGATATTTTCCGATGCCTCCTCCTAGCGTC
       E  E  S  R  S  F  F  Y  K  R  L  R  R  I  A  E

AAGATGTTCTTGCAAAAGAAATAAGGCAGATAGTCGGTGATAAATTTACG
3601  --------+---------+---------+---------+---------+  3650
      TTCTACAAGAACGTTTTCTTTATTCCGTCTATCAGCCACTATTTAAATGC
        D  V  L  A  K  E  I  R  Q  I  V  G  D  K  F  T

CACCAATTAGCAATGGAGCTCATCAAGGAATGGTACCTTGCTTCTCAGGC
3651  --------+---------+---------+---------+---------+  3700
      GTGGTTAATCGTTACCTCGAGTAGTTCCTTACCATGGAACGAAGAGTCCG
       H  Q  L  A  M  E  L  I  K  E  W  Y  L  A  S  Q  A

CACAACAGGAAGCACTGGATGGGATGACGATGATGCTTTTGTTGCCTGGA
3701  --------+---------+---------+---------+---------+  3750
      GTGTTGTCCTTCGTGACCTACCCTACTGCTACTACGAAAACAACGGACCT
        T  T  G  S  T  G  W  D  D  D  D  A  F  V  A  W  K

AGGACAGTCCTGAAAACTACAAGGGGCATATCCAAAAGCTTAGGGCTCAA
3751  --------+---------+---------+---------+---------+  3800
      TCCTGTCAGGACTTTTGATGTTCCCCGTATAGGTTTTCGAATCCCGAGTT
         D  S  P  E  N  Y  K  G  H  I  Q  K  L  R  A  Q

AAAGTGTCTCATTCGCTCTCTGATCTTGCTGACTCCAGTTCAGATCTGCA
3801  --------+---------+---------+---------+---------+  3850
      TTTCACAGAGTAAGCGAGAGACTAGAACGACTGAGGTCAAGTCTAGACGT
       K  V  S  H  S  L  S  D  L  A  D  S  S  S  D  L  Q

AGCATTCTCGCAGGGTCTTTCTACGCTATTAGATAAGATGGATCCCTCTC
3851  --------+---------+---------+---------+---------+  3900
      TCGTAAGAGCGTCCCAGAAAGATGCGATAATCTATTCTACCTAGGGAGAG
       A  F  S  Q  G  L  S  T  L  L  D  K  M  D  P  S  Q

AGAGAGCGAAGTTTGTTCAGGAAGTCAAGAAGGTCCTTGATTGATGATAC
3901  --------+---------+---------+---------+---------+  3950
      TCTCTCGCTTCAAACAAGTCCTTCAGTTCTTCCAGGAACTAACTACTATG
         R  A  K  F  V  Q  E  V  K  K  V  L  D  *  *

CAACACATCCAACACAATGTGTGCATGTCACATCTTTTGTTCTAGTACA
3951  --------+---------+---------+---------+---------+  4000
      GTTGTGTAGGTTGTGTTACACACGTACAGTGTAGAAAACAAGATCATGT
```

FIG. 3(j)

```
        TACATAGAAGGATATTGCTTGGTCTTGATTGATCATGTCTGATTTAAGTC
4001    ----------+---------+---------+---------+---------+    4050
        ATGTATCTTCCTATAACGAACCAGAACTAACTAGTACAGACTAAATTCAG

GACTATTATTTCTTGGAATTTTCTTTTGGACCTGGTGCTATGGTTGATGG
4051    ----------+---------+---------+---------+---------+    4100
        CTGATAATAAAGAACCTTAAAAGAAAACCTGGACCACGATACCAACTACC

ATGTATATTGGATATGTGCGTTCTGCCAGGTGTAAGCACAAAGGTTTAGA
4101    ----------+---------+---------+---------+---------+    4150
        TACATATAACCTATACACGCAAGACGGTCCACATTCGTGTTTCCAAATCT

CAGACCGAGAGCAAGAGCGAGTGAACCTGTTCTGGTTTTGCAGTGGTTCA
4151    ----------+---------+---------+---------+---------+    4200
        GTCTGGCTCTCGTTCTCGCTCACTTGGACAAGACCAAAACGTCACCAAGT

GTAAGGCAGAAAGTTGTTAAACCGTAGTTCTGAGATGTATTACCAGTGGC
4201    ----------+---------+---------+---------+---------+    4250
        CATTCCGTCTTTCAACAATTTGGCATCAAGACTCTACATAATGGTCACCG

GCCATGCTGTACTTTTAGGGTGTATAATGCGGATACAAATAAACAATTTA
4251    ----------+---------+---------+---------+---------+    4300
        CGGTACGACATGAAAATCCCACATATTACGCCTATGTTTATTTGTTAAAT

GCGGTTCATTAAAGTTTGAACTCAAATAAAAAAAAAAAAAAAAAAA
4301    ----------+---------+---------+---------+------         4346
        CGCCAAGTAATTTCAAACTTGAGTTTATTTTTTTTTTTTTTTTTT
```

FIG. 4(a)

```
        CAAATACACAATTGAATCTGTAAGGACTGGACATGGTAGCTACAGGTTGA
  1     ----------+---------+---------+---------+---------+     50
        GTTTATGTGTTAACTTAGACATTCCTGACCTGTACCATCGATGTCCAACT
         K  Y  T  I  E  S  V  R  T  G  H  G  S  Y  R  L  R

GAGTGAATGATTCAACAGTTGAAGCGAATGTACAATCTTTATGTGATGGT
 51     ----------+---------+---------+---------+---------+    100
        CTCACTTACTAAGTTGTCAACTTCGCTTACATGTTAGAAATACACTACCA
          V  N  D  S  T  V  E  A  N  V  Q  S  L  C  D  G

GGCCTCTTAATGCAGTTGGATGGAAACAGCCATGTAATTTATGCAGAAGA
101     ----------+---------+---------+---------+---------+    150
        CCGGAGAATTACGTCAACCTACCTTTGTCGGTACATTAAATACGTCTTCT
         G  L  L  M  Q  L  D  G  N  S  H  V  I  Y  A  E  E

AGAAGCTGGTGGTACACGGCTTCAGATTGATGGAAAGACATGTTTATTGC
151     ----------+---------+---------+---------+---------+    200
        TCTTCGACCACCATGTGCCGAAGTCTAACTACCTTTCTGTACAAATAACG
          E  A  G  G  T  R  L  Q  I  D  G  K  T  C  L  L  Q

AGAATGACCATGATCCATCAAAGTTATTAGCTGAGACACCCTGCAAACTT
201     ----------+---------+---------+---------+---------+    250
        TCTTACTGGTACTAGGTAGTTTCAATAATCGACTCTGTGGGACGTTTGAA
           N  D  H  D  P  S  K  L  L  A  E  T  P  C  K  L

CTTCGTTTCTTGGTTGCTGATGGTGCTCATGTTGATGCGGATGTACCATA
251     ----------+---------+---------+---------+---------+    300
        GAAGCAAAGAACCAACGACTACCACGAGTACAACTACGCCTACATGGTAT
         L  R  F  L  V  A  D  G  A  H  V  D  A  D  V  P  Y

CGCGGAAGTTGAGGTTATGAAGATGTGCATGCCTCTCTTGTCACCTGCTT
301     ----------+---------+---------+---------+---------+    350
        GCGCCTTCAACTCCAATACTTCTACACGTACGGAGAGAACAGTGGACGAA
          A  E  V  E  V  M  K  M  C  M  P  L  L  S  P  A  S

CTGGTGTCATTCATTGTATGATGTCTGAGGGCCAGGCATTGCAGGCTGGT
351     ----------+---------+---------+---------+---------+    400
        GACCACAGTAAGTAACATACTACAGACTCCCGGTCCGTAACGTCCGACCA
           G  V  I  H  C  M  M  S  E  G  Q  A  L  Q  A  G
```

FIG. 4(b)

```
     GTTGAATTTTTACCATGGAAAAAACGAGGACTTTCCATCCAAGTTGCTAA
 1   ---------+---------+---------+---------+---------+   50
     CAACTTAAAAATGGTACCTTTTTGCTCCTGAAAGGTAGGTTCAACGATT
       L  N  F  Y  H  G  K  N  E  D  F  P  S  K  L  L  R

GAGACATCATTGAGGAAAATCTTTCTTATGGTTCAGAGAAGGAAAAGGCT
51   ---------+---------+---------+---------+---------+   100
     CTCTGTAGTAACTCCTTTTAGAAAGAATACCAAGTCTCTTCCTTTTCCGA
        D  I  I  E  E  N  L  S  Y  G  S  E  K  E  K  A

ACAAATGAGAGGCTTGTTGAGCCTCTTATGAACCTACTGAAGTCATATGA
101  ---------+---------+---------+---------+---------+   150
     TGTTTACTCTCCGAACAACTCGGAGAATACTTGGATGACTTCAGTATACT
        T  N  E  R  L  V  E  P  L  M  N  L  L  K  S  Y  E

GGGTGGGAGAGAGAGCCATGCACATTTTGTTGTCAAGTCTCTTTTCGAGG
151  ---------+---------+---------+---------+---------+   200
     CCCACCCTCTCTCTCGGTACGTGTAAAACAACAGTTCAGAGAAAAGCTCC
        G  G  R  E  S  H  A  H  F  V  V  K  S  L  F  E  E

AGTATCTTACAGTGGAAGAACTTTTTAGTG
201  ---------+---------+---------+   230
     TCATAGAATGTCACCTTCTTGAAAAATCAC
        Y  L  T  V  E  E  L  F  S
```

FIG.5(a)

```
     GTTCAAGCTGAGAGGCCCCCATGGTATATCTCAGTGGTTGGAGGTgCTTT
  1  ----------+----------+----------+----------+----------+  50
     CAAGTTCGACTCTCCGGGGGTACCATATAGAGTCACCAACCTCCAcGAAA
      V  Q  A  E  R  P  P  W  Y  I  S  V  V  G  G  A  L

ATATAAAACAGTAACCACCAATGCAGCCACTGTTTCTgAATATGTTAGTT
 51  ----------+----------+----------+----------+----------+  100
     TATATTTTGTCATTGGTGGTTACGTCGGTGACAAAGAcTTATACAATCAA
       Y  K  T  V  T  T  N  A  A  T  V  S  E  Y  V  S  Y

ATCTCACCAAAGGCCAGATTCCACCAAAGCATATATCCCTTGTCAATTCA
101  ----------+----------+----------+----------+----------+  150
     TAGAGTGGTTTCCGGTCTAAGGTGGTTTCGTATATAGGGAACAGTTAAGT
        L  T  K  G  Q  I  P  P  K  H  I  S  L  V  N  S

ACAGTtAATTTGAATATAGAAGGGAGCAAATACACAATTGAAACTgTCAG
151  ----------+----------+----------+----------+----------+  200
     TGTCAaTTAAACTTATATCTTCCCTCGTTTATGTGTTAACTTTGAcAGTC
      T  V  N  L  N  I  E  G  S  K  Y  T  I  E  T  V  R

GACTGGGCATGGTAGGTACAAGTTGCGAATGAATGATTCAACAGTTGAGG
201  ----------+----------+----------+----------+----------+  250
     CTGACCCGTACCATCCATGTTCAACGCTTACTTACTAAGTTGTCAACTCC
       T  G  H  G  R  Y  K  L  R  M  N  D  S  T  V  E
```

FIG. 5(b)

```
    TATGGTTCAGAGAAGGAAAAGGCTACAAATGAGCGACTTGTTGAGCCTCT
 1  --------+---------+---------+---------+---------+  50
    ATACCAAGTCTCTTCCTTTTCCGATGTTTACTCGCTGAACAACTCGGAGA
     Y  G  S  E  K  E  K  A  T  N  E  R  L  V  E  P  L

TATGAACCTACTGAAGTCATATGAGGGTGGGAGAGAAAGCCATGCACATT
 51 --------+---------+---------+---------+---------+ 100
    ATACTTGGATGACTTCAGTATACTCCCACCCTCTCTTTCGGTACGTGTAA
       M  N  L  L  K  S  Y  E  G  G  R  E  S  H  A  H  F

TTGTTGTCAAGTCTCTTTTTGAGGAGTATCTTACCGTGGAAGAACTTTTC
101 --------+---------+---------+---------+---------+ 150
    AACAACAGTTCAGAGAAAAACTCCTCATAGAATGGCACCTTCTTGAAAAG
        V  V  K  S  L  F  E  E  Y  L  T  V  E  E  L  F

AGTGATGGCATTCAGTCTGACGTGATTGAAACCTTGCGTCATCAGCACAG
151 --------+---------+---------+---------+---------+ 200
    TCACTACCGTAAGTCAGACTGCACTAACTTTGGAACGCAGTAGTCGTGTC
      S  D  G  I  Q  S  D  V  I  E  T  L  R  H  Q  H  S

TAAAGACCTGCAGAAGGTTGTAGACATCGTGCTGTCTCACCAGGGTGTGA
201 --------+---------+---------+---------+---------+ 250
    ATTTCTGGACGTCTTCCAACATCTGTAGCACGACAGAGTGGTCCCACACT
      K  D  L  Q  K  V  V  D  I  V  L  S  H  Q  G  V  R

GGAACAAAGCTAAGCTTGTAACAGCACTTATGGAAAAGCTGGTTTATCCA
251 --------+---------+---------+---------+---------+ 300
    CCTTGTTTCGATTCGAACATTGTCGTGAATACCTTTTCGACCAAATAGGT
       N  K  A  K  L  V  T  A  L  M  E  K  L  V  Y  P

AATCCTGCATTGCAAGAAGCCTTTCAGATC
301 --------+---------+---------+ 330
    TTAGGACGTAACGTTCTTCGGAAAGTCTAG
      N  P  A  L  Q  E  A  F  Q  I
```

FIG.5(c)

```
     TGCTTGCCCCTTGATTGACCATGTCTGATCCTAAGTCGACCATTATTTCC
  1  ---------+---------+---------+---------+---------+  50
     ACGAACGGGGAACTAACTGGTACAGACTAGGATTCAGCTGGTAATAAAGG

TTGAAACTTCCTTTCGGACGTGGTGCTATGGTTGATGAATTTGGATGTGT
 51  ---------+---------+---------+---------+---------+  100
     AACTTTGAAGGAAAGCCTGCACCACGATACCAACTACTTAAACCTACACA

GCGTTCTGCCAGGTGTAAGCCCAAAGGTTTATACAGACCGAGTTAAGGTT
101  ---------+---------+---------+---------+---------+  150
     CGCAAGACGGTCCACATTCGGGTTTCCAAATATGTCTGGCTCAATTCCAA

AGGAAGAGCACGAGTGAACCTGTTCTGGTTTTGCAGTGGTTAAGGCAGAA
151  ---------+---------+---------+---------+---------+  200
     TCCTTCTCGTGCTCACTTGGACAAGACCAAAACGTCACCAATTCCGTCTT

AGTTGTTTCACTGTAGTTCTGAGATGTATTACCAGCGGCGCTGTAATTTT
201  ---------+---------+---------+---------+---------+  250
     TCAACAAAGTGACATCAAGACTCTACATAATGGTCGCCGCGACATTAAAA

AGGGTGTATAATGCGGATGCTAGTAAACAATTGAGTGGTTCTTTAAAAAA
251  ---------+---------+---------+---------+---------+  300
     TCCCACATATTACGCCTACGATCATTTGTTAACTCACCAAGAAATTTTTT

AAAAAAAAAAAAAAAAAAA
301  ---------+--------  319
     TTTTTTTTTTTTTTTTTTT
```

MAIZE ACETYL COA CARBOXYLASE ENCODING DNA CLONES

FIELD OF THE INVENTION

The present invention relates to novel DNA clones and uses thereof: including the use thereof to transform plants and genetically modified plants so obtained.

SUMMARY OF THE INVENTION

Clones according to the present invention comprise at least part of a DNA sequence of a gene encoding maize acetyl CoA carboxylase, or a sequence showing substantial homology therewith, flanked by heterologous DNA.

Acetyl CoA carboxylase (ACCase), a biotin-containing enzyme, catalyses the first step in the fatty acid biosynthesis pathway, namely the carboxylation of acetyl CoA to give malonyl CoA. Accordingly clones according to the invention have a number of uses, depending on their exact nature.

For example, clones according to the invention containing partial coding sequences of an ACCase gene may be used to probe plant DNA (for example genomic DNA, or cDNA libraries prepared from messenger RNA) to obtain other clones according to the invention. These other clones may be different or longer; they may be substantially complete clones of the maize ACCase, or part or all of genes coding for corresponding or similar enzymes in maize or other plants (both monocots and dicots). Partial sequences according to the invention may be used (generally but not necessarily in reverse orientation) in combination with a regulator sequence functional in plants to construct an expression cassette. This expression cassette can then be used to transform plants to down-regulate the production of ACCase enzyme. This can alter the composition of seed or other plant parts, for example enabling oil-bearing plants (oilseed rape, sunflower, oilpalm) having a lower or otherwise modified oil content to be produced.

Clones containing longer or substantially complete sequences of an ACCase gene may also be used to form similar expression cassettes. Such coding sequences may be used in plants (either by using more powerful promoters or by inserting extra copies of the gene) to promote the expression or overexpression of ACCase, for example leading to plants with an enhanced oil content.

Partial clones according to the invention can be used to probe plant DNA to recover the promoter of the ACCase gene. This promoter may then be used to generate RNA in a tissue-specific or developmentally-regulated fashion. The RNA so generated may inhibit expression of ACCase, or another gene; or be mRNA that generates ACCase, or another protein.

In monocotyledonous plants the ACCase enzyme is inhibited by certain classes of grass-weed herbicides (aryloxyphenoxypropionates such as fluazifop, alkylketones) whereas in dicots the enzyme is relatively tolerant to these herbicides. Accordingly in a further aspect the present invention comprises monocotyledonous plants resistant to herbicides active by interfering with the fatty acid synthesis pathway, said plants having been obtained by transformation with constructs according to the invention adapted to express ACCase enzyme. Such plants may be made resistant in various ways, for example:

1. By overexpression of monocotyledonous ACCase for example using powerful promoters or multiple gene insertions;
2. By expression of dicotyledonous ACCase;
3. Possibly, by expression of a resistant form of maize ACCase. The gene for resistant maize ACCase might be obtained by mutagenesis and selection in a suitable host or by tissue culture of the plant in the presence of the appropriate herbicide.

The purpose in providing crop plants which resist the action of a herbicide is to facilitate the destruction of weeds growing between the plants by the overall application of a herbicidally effective concentration of a herbicide which would destroy the crop plant in its normal, that is herbicide-sensitive, state. Such resistant plants are also useful where there has been any short term carry-over of herbicide from a previous crop. The development of crops with novel types of herbicide resistance is agronomically useful, giving the farmer additional options to obtain an improved harvest by means which may be safer, cheaper or more effective than those currently available. In the present case, rendering maize or small-grain cereals such as wheat and barley resistant to the herbicide fluazifop would enable this herbicide to be used to combat wild oats in these crops—a very effective advance over what is available at present.

We have prepared clones according to the invention by extracting ACCase from plant material, purifying it, preparing antibodies thereto by challenging a mammalian immune system therewith, immuno-purifying the antibodies and using them to select clones from a plant DNA library. Clones A3 and A4 prepared by this process (designated A3 ACC cDNA and A4 ACC cDNA, respectively) were deposited on 13 Nov. 1991 with the Australian Government Analytical Laboratory, 1 Suakin Street, Pymble NSW2073.

Accordingly, a simpler process for the preparation of clones according to the invention comprises reproducing the clones designated A3 ACC cDNA and A4 ACC cDNA available from the Australian Government Analytical Laboratory, or relatives or descendants of such clones.

BRIEF DESCRIPTION OF THE DRAWINGS

The invention will now be further described with reference to the following Examples, and to the drawings, in which:

FIGS. 3(a) to 3(j), taken together, are the nucleotide and deduced amino acid sequence of the A3 ACC cDNA maize clone (SEQ ID NO:1 and SEQ ID NO:2);

FIGS. 4a–4b are the nucleotide sequence and deduced amino acid sequence of the 5' ends of the A3-like clones A10 (a) and A34 (b) (SEQ ID NO:3 through SEQ ID NO:6);

FIGS. 5a–5c are the nucleotide sequence and deduced amino acid sequence of the 5' ends of the A4-like clones A12 (a), A4 (b) and the 3' end of A12 (c) (SEQ ID NO:7 through SEQ ID NO:11).

DESCRIPTION OF PREFERRED EMBODIMENTS

Figures 1A, 1B:
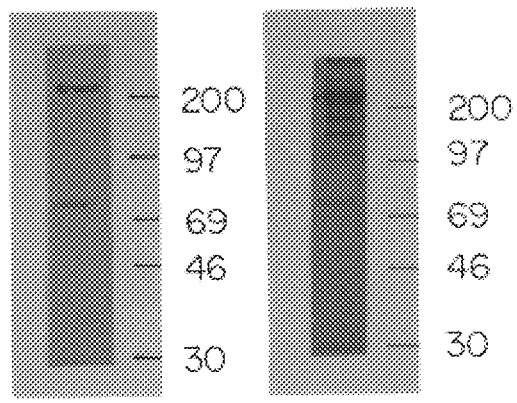
FIGS. 1a–1b are an SDS-PAGE diagram of partially purified maize ACCase, in which Lane A is a Coomassie Blue stained gel, and lane B is a streptavidin-phosphatase treated electroblot of ACCase showing the presence of biotin-containing polypeptides.

In the Examples we describe the use of affinity purified antibodies to maize ACCase to select clones from a maize cDNA expression library; and we show that three of the clones obtained encode maize ACCase. Confirmatory evidence for the identity of the clones is as follows:

(i) amino acid sequences, deduced from DNA sequencing of one of the clones, were found to be up to 50% identical with parts of the rat and chicken ACCase sequence.

(ii) the longest cloned cDNA insert (4.5 kb) is considerably longer than the predicted length of any mRNA encoding known biotin-containing enzymes in plants, other than that encoding ACCase.

We believe that the A3 and A4 clones represent two different maize ACCase genes. We have also found that the maize ACCase clones hybridise to Southern blots of Arabidopsis DNA. This enables us to obtain from such Arabidopsis DNA probes suitable for isolation of ACC-type coding sequences and genes from other plants, both dicots and monocots.

Material and Methods

Partial Purification of Acetyl CoA Carboxylase From Maize Leaves

Plant Material. Seedlings of maize (*Zea mays* Dekalb XL81) were grown in sterile soil, in a glasshouse with the temperature maintained between 20° C. and 30° C. under natural illumination. Leaves of 2 to 4 week old plants were used for enzyme preparation.

Purification. Extraction and purification procedures were carried out at 0°–4° C.

Extraction. Leaf material (160 g) was homogenised in a Waring blender with 300 ml of medium consisting of 0.1M Tris-HCl buffer (pH 8.0), 10 mM $MgCl_2$, 1 mM EDTA, 20 mM 2-mercaptoethanol, 0.2 mM PMSF, 2 mM benzamidine hydrochloride, and 2% (w/v) of polyvinylpolypyrrolidone. The homegenate was filtered through two layers of muslin and two layers of Miracloth and the filtrate (380 ml) centrifuged at 13000 g for 30 minutes.

Ammonium sulphate and polyethylene glycol fractionation steps. To the centrifuged extract (365 ml) was added sufficient solid ammonium sulphate with stirring to bring the mixture to 40% saturation. After 40 minutes gentle stirring the mixture was centrifuged at 13000 g for 30 minutes and the supernatant discarded. The protein pellet was re-dissolved in a medium consisting of 20 mM Tris-HCl (pH 8.0) 10 mM $MgCl_2$, 1 mM EDTA, 10 mM dithiothreitol, 0.2 mM PMSF, and 10% (v/v) glycerol. To this solution (204 ml) was added solid PEG (8 g per 100 ml) with stirring. After 40 minutes gentle stirring the suspension was centrifuged as above and the pellet discarded. More PEG was added to the supernatant (12 g per 100 ml) and, after stirring for 40 minutes, the mixture was again centrifuged and the pellet kept.

Affinity chromatography on Matrix gel Orange A. The precipitated protein was re-dissolved in buffer consisting of 20 mM Hepes KOH (pH 6.8), 10 mM $MgCl_2$, 1 mM EDTA, 10 mM DTT, and 10% (v/v) glycerol and clarified at 10000 g for 20 minutes. The supernatant (100 ml) was passed through a 40 ml column of orange A gel (previously equilibrated with column buffer consisting of the above dissolving medium but containing 20 mM 2-mercaptoethanol instead of DTT) at a flow rate of approximately 0.4 ml per minute. The column was then washed with 800 ml of column buffer at about 1 ml per minute to remove unbound protein. Acetyl CoA carboxylase was subsequently eluted from the column with 100 ml of 0.5 mM CoA in dissolving buffer followed by more buffer. Fractions containing acetyl CoA carboxylase activity were pooled (100 ml) and concentrated by ultrafiltration over a PM30 membrane (Amicon Scientific) to a volume of 5.8 ml. The enzyme solution was divided into aliquots and rapidly frozen (in liquid nitrogen) before storage at –80° C.

Measurement of Enzyme Activity

Acetyl CoA carboxylase activity was measured at 30° C. by the enzyme and substrate dependent incorporation of radioactivity from $NaH^{14}CO_3$ into acid-stable products, based on published methods. Reaction mixtures contained (in a total volume of 200 μl): 100 mM Tris-HCl (pH 8.0), 50 mm KCl, 5 mm $MgCl_2$, 5 mM DTT, 2 mM ATP, 15 mM $NaH^{14}CO_3$ approx. 0.25 Ci per mole), 0.75 mM acetyl CoA (trilithium salt), and enzyme (2–10 mU). Reactions were initiated with enzyme and stopped after 6 minutes by adding 50 μl of 6M HCl. Portions of the reaction mixture were spotted into filter paper discs, which were then dried and the acid-stable $^{14}C$ reaction products measured by scintillation counting. The amount of enzyme which catalyses conversion of 1 μmol of substrate per min is defined as 1 unit.

Protein Determination

Protein concentration was measured by Coomassie Blue dye binding according to published methods and using bovine serum albumin as standard.

SDS-Polyacrylamide Gel Electrophoresis/electroblotting

SDS-PAGE and electroblotting to nitro-cellulose or PVDF membranes were carried out according to published methods.

Electrophoretic Isolation of ACCase Subunit 3.7 ml of a preparation of ACCase (partially purified essentially by the above procedure) containing about 680 μg of protein were concentrated to 100 μl using centrifugal filters (Amicon Centricon 100). The concentrated protein solution was added to 80 μl of a digestion mixture containing 125 mM Tris-HCl (pH 6.7), 2% (w/v) SDS, 10% (w/v) glycerol and 0.01% (w/v) bromophenol blue, and the solution heated at 98° C. for 5 minutes. The digest was applied to several tracks of a 7.5% polyacrylamide gel and the protein subunits separated by SDS-PAGE. The gel was subsequently washed with 5 mM Tris-HCl (pH 6.7) then stained with Coomassie Blue G (1% w/v in water) before destaining with water. Segments of the stained gel containing ACCase subunit were cut out.

Chemical Cleavage of ACCase Subunit and Isolation of Fragments

Gel segments containing ACCase subunit were gently agitated in 4 ml of UHA (urea/water/acetic acid; 25 g:25 ml:25 ml) for 80 min with one change of solution. The segments were then treated with 4 ml of a solution of 0.2% (w/v) N-chlorosuccinimide in UHA for 60 minutes to cleave the ACCase subunit at tryptophan residues, followed by washing with 5 mM Tris HCl, pH 6.7 (30 min). The gel segments were then equilibrated with a solution containing 125 mM Tris-HCl (pH 6.7), 5% (w/v) PEG, 20 mM DTT, 1% (w/v) SDS, for 90 min, finally heating the segments in solution to 95° C. for 6 min. The gel segments, containing cleaved fragments of ACCase subunit, were then loaded onto several tracks of a 16% acrylamide gel and the fragments separated by SDS-PAGE. After separation, the polypeptide fragments were electroblotted onto a PVDF membrane by published methods and the membrane stained with Amido black. Portions of the membrane containing major polypeptide fragments were excised and destained exhaustively with 10 mM Tris base, then washed with water before being submitted for N-terminal amino acid sequencing.

N-terminal Amino Acid Sequencing

N-terminal amino acid sequencing was carried out by established techniques at the Biomolecular Resources Facility of the Australian National University.

Production of Antibodies to Maize ACCase

Orange A-purified maize ACCase (~50 μg protein in 1 ml Freund's complete adjuvant) was injected into the hind leg muscle of a rabbit. Four weeks later a further 50 μg of the maize ACCase in incomplete Freund's adjuvant was similarly injected. The rabbit was bled at two to three week intervals and serum collected. The first serum sample did not contain detectable antibodies to maize ACCase as judged by binding to maize ACCase after SDS-PAGE and immunoblotting or inhibition of maize ACCase activity. The second and subsequent bleedings yielded antiserum that bound to maize ACCase as judged by the two criteria listed above. This antiserum was used as the starting material for purification of affinity-purified antibody.

Affinity-purification of Antibodies to Maize ACCase

Partially purified maize ACCase (500 μl) was resolved from contaminants by preparative SDS polyacrylamide gel electrophoresis. The membranes were stained with Amido Black and the ACCase band at ~200 kDa was cut out. Residual adsorption sites on the membrane were blocked by incubation of the membrane in TBS (20 mM Tris-KCl, pH 7.5, 150 mM NaCl) containing 5% (w/v) powdered milk. Antibodies to maize ACCase were adsorbed to the membrane by incubating the ACCase-coated membrane in 1 ml dilute antiserum (0.5 ml antiserum 0.5 ml TBS) at room temperature for 1 hour. The membrane was removed, washed for 5 minutes in 10 ml TBS+0.05% Tween 20 then twice (5 min each) in 10 ml TBS. The membrane-bound antibodies were eluted by incubation with 1 ml 0.1M glycine/HCl pH2.6 for 3 minutes and neutralised. This cycle of adsorption and elution was repeated two more times using the same membrane and antiserum.

Before use the affinity-purified antibody was diluted to 20 ml with TBS. This antibody preparation was further depleted of non-specific antibodies by incubation with nitro-cellulose coated with an $E.\ coli$ $\lambda$ phage lysate. Finally, the affinity-purified antibody was made 10% with respect to horse serum albumin to further minimise non-specific binding.

Immunoprecipitation of ACCase by Rabbit Antiserum

A series of dilutions of serum from control and ACCase-immunised rabbits were prepared. Enzyme extract (50 μl) supplemented with 0.02% (v/v) Triton X-100 was mixed with diluted serum (50 μl) and incubated at 30° C. For maize, the enzyme was Orange-A purified while for $Amaranthus\ edulis$ a G-25 treated crude leaf extract prepared from 1 g of tissue in 2 ml of solution containing 0.1M Tris-HCl (pH 8.0), 10 mM $MgCl_2$, 1 mM EDTA, 10 mM DTT, 0.01% (v/v) Triton X-100 was used. After 50 minutes incubation of serum with maize enzyme, immune complexes were removed by adding 20 μl of a suspension of Protein A-Sepharose (0.2 g per ml in 0.1M $KH_2PO_4$ buffer pH 7.0) and centrifuging (11600 g, 5 min) after a further 60 min at room temperature. Enzyme activity remaining in the supernatant was measured. Incubation of $Amaranthus\ edulis$ extract with serum was for 160 min before removal of immunoprecipitates with Protein A and centrifugation (5 min, 11500 g). The $A.\ endulis$ mixtures were left a further 16 hours at 4° C. and centrifuged again before assay of remaining enzyme in the supernatant.

Maize Leaf cDNA Library

This was a gift from Dr A Barkan, Department of Botany, University of California, Berkeley. Messenger RNA was isolated from leaves of two week old $Zea\ mays$ (B73) seedlings. cDNA was synthesised using a ZAP cDNA synthesis kit (Stratagene). The cDNA was ligated into the EcoRI site (5' end of the cDNA) and the XhoI site (3' end of the cDNA) of lambda expression vector $\lambda$ZAP. The library contained $8 \times 10^5$ recombinants.

Screening of Maize cDNA Library

The maize $\lambda$ZAP cDNA library was screened for clones producing fusion proteins that would bind to antibodies purified by adsorption to purified maize ACCase.

Phage was adsorbed to $E.\ coli$ Y1090 cells mixed with 0.8% agarose/10 mm $MgSO_4$/0.02% maltose in LB, plated at a density of about 100 plaques $cm^2$. The plates were incubated at 37° C. for about 4 hours; then nitro-cellulose filters impregnated with IPTG were placed on the agarose surface and the incubation continued at 37° C. overnight. The filters were removed, washed in TBS buffer containing 5% (w/v) powdered milk to block the surface of the nitrocellulose before screening with affinity purified antibody. The filters (6×137 mm diam) were incubated in 20 ml of the affinity purified antibody for 2 hours at room temperature. The filters were washed in TBS containing 0.05% Tween 20 three times, then in goat anti-rabbit immunoglobulin coupled to alkaline phosphatase (1:7500 in TTBS, 0.2% Tween 20 in TBS) for 1 hour at room temperature. The filters were freed of unbound 2nd antibody by washing twice in TTBS then once in TBS. The plaques expressing ACCase-fusion proteins were visualised by incubating on an alkaline phosphatase reaction mixture containing BCPIP and NBT (150 μl/ml BCPIP, 150 μl/ml NBT in 100 mM Tris-Hcl, pH 9.5, 100 mM NaCl, 1 mm $MgCl_2$). Plaques giving a positive reaction were further purified by repeated rounds of screening using the same antibody solution until all plaques on a plate gave a positive signal. Three positive plaques were obtained by this procedure.

Results

Following the procedure detailed above, ACCase was purified over 100-fold from maize leaves to a specific activity of 3–4 units per mg protein (Table 1). Analysis by SDS-PAGE of the enzyme at different stages of purification showed that ACCase consisted of polypeptide subunits of about 200–220 kDa and, at the final stage, was about 70% pure (FIG. 1). The presence of biotin in the ACCase subunit was demonstrated by Western blotting of the SDS-polyacrylamide gel and assaying with streptavidin-phosphatase. A number of degradation products of ACCase were also shown by this sensitive procedure.

Attempts to determine the N-terminal amino acid sequence were unsuccessful, presumably because it was blocked. However, limited internal sequence data has been by cleaving the electrophoretically purified subunit with N-chlorosuccinimide, re-electrophoresing the products and electroblotting to PVDF membrane for N-terminal sequence analysis. The three sequences obtained were 8,4 and 8 amino acids in length and were 62.5%, 100% and 75% similar to sequences in chicken ACCase (Table 2).

Orange-A purified ACCase was injected into a rabbit and, following two booster injections, the rabbit serum was found to form immune complexes with maize ACCase activity. ACCase activity from Amaranthus was also immunoprecipitated by similar concentrations of antiserum.

ACCase antibodies were affinity purified by adsorption to and elution from a PVDF membrane containing electrophoretically purified ACCase subunit. This purified antibody preparation was used to screen the maize cDNA expression library.

Isolation of Maize ACCase cDNA Clones

Approximately 90,000 plaques of a maize cDNA expression library constructed in the vector λZAP (Strategene) were screened with affinity-purified ACCase antibody. Of the seven clones picked in the primary screening, three remained positive through two further rounds of purification. Two of these (A1 and A3) gave a much stronger signal than the third (A4).

Analysis of the Bluescript phagemids released from the λZAP clones indicated they were carrying DNA inserts of 4.0 (A1), 4.4 (A3) and 4.4 (A4) kb. Restriction mapping showed the 4.0 and 4.4 kb inserts of A1 and A3 to be almost identical, except for the extra 400 bp at the 5' end. The map of A4 was different but the A4 insert cross-hybridised to A1/A3.

Figure 2:
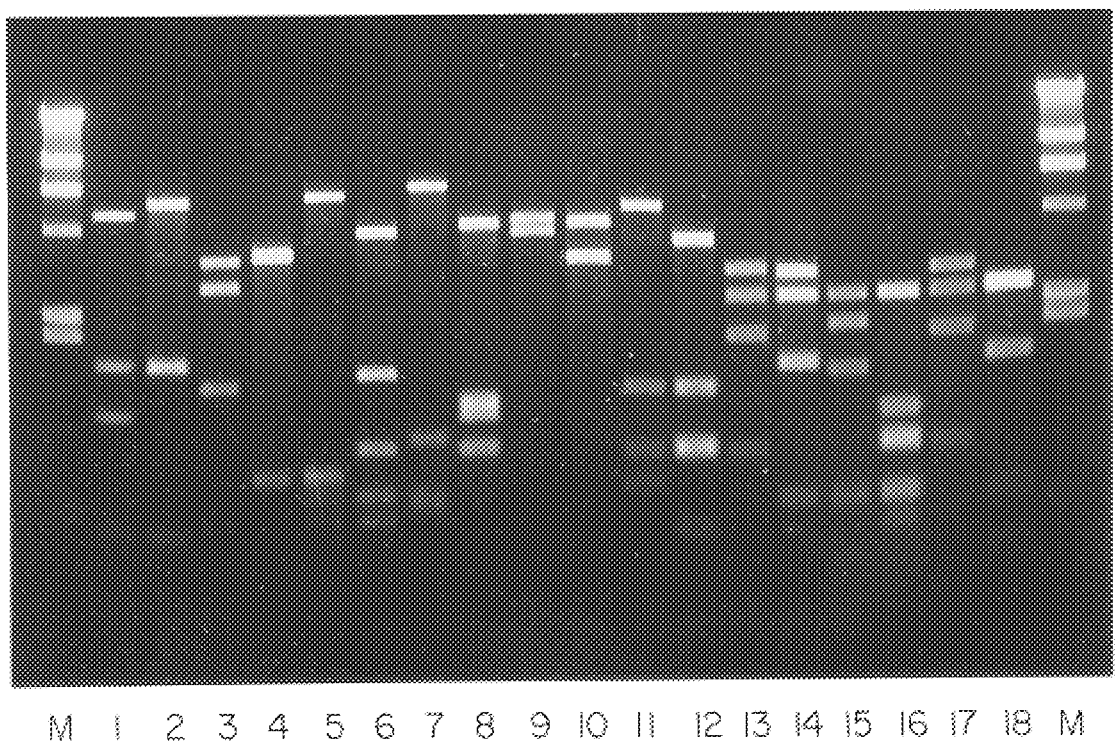
FIG. 2 compares the digestion patterns of an A4-like cDNA (A12) and an A3-like cDNA (A34) cut with a number of different restriction enzymes; the odd numbered lanes show ACC12 and the even numbered lanes show ACC34. The enzymes used are Pst1 (1,2), BamH1+Bg1II (3,4), HindIII (5,6), HincII (7,8), EcoR1 (9,10), AccI (11,12), PvuII (13,14), PvuII+HincII (15,16), PvuII+EcoRV (17,18). Marker lanes are λ DNA digested with HindIII.

Re-screening of the λZAP library with the A3 insert yielded a further six positively hybridising clones. Restriction mapping established that four of these were like A1/A3 and two were like A4. FIG. 2 shows the digestion pattern for an A4-like cDNA (A12) and an A3-like cDNA (A34) cut with a number of different restriction enzymes. These results indicate there are at least two genes for ACCase in maize.

The DNA sequence of the A3 ACC cDNA clone was determined (FIG. 3). The deduced amino acid sequence was 37% identical (58% similar) to the rat/chicken ACCase sequence and, over one stretch of 100 residues, the sequences were more than 60% identical.

The sequence of most of the A1 ACC cDNA was determined and found to be identical to the A3 sequence. Additional sequence information for the 5' ends of longer A3-like clones are given in FIGS. 4($a,b$). In the case of clone A10/A49, the sequence includes the motif that encodes the conserved biotin-binding site, met-lys-met (FIG. 4$b$) of ACCase.

Analysis of the 5' ends of two A4-like clones, A12 and A4 ACC cDNAs (FIGS. 5$a,b$), and of the 3' end of A12 (FIG. 5$c$) showed there are a significant number of differences between the sequences of A3- and A4-like cDNAs. This supports the conclusion drawn from the restriction digest patterns that there must be at least two ACCase genes in maize.

Hybridisation of the A3 cDNA to Southern blots of EcoR1 and BamH1 digested maize DNA gave 3 and 2 bands respectively. It is likely therefore that there are no more than two ACCase genes in maize. The maize cDNA also hybridised to Arabidopsis DNA under low stringency conditions.

Hybridisation of the A3 cDNA insert to a northern blot of maize RNA gave just one band of size 8.0–8.5 kb.

Discussion

The size of the maize ACCase subunit (~220 kDa) is similar to that of the enzyme from rat and chicken. The mRNA for such a protein would be expected to be at least 6.5 kb and according to our determination is in fact 8.0–8.5 kb for maize. This is considerably longer than the longest cDNAs (5.5 kb for A3-like and 5.7 kb for A4-like clones) described here. These cDNAs, however, will provide the means for isolating full-length cDNAs. The cDNAs may be used as primers for 5' extension against maize mRNA as a template or as probes for isolating the genes from a maize genomic library.

The maize ACCase cDNA cross-hybridised to Arabidopsis DNA and it therefore presents a means for isolating the gene from an Arabidopsis genomic library. The same heterologous probe may be used for isolating ACCase genes from a range of plants, including both monocots and dicots, for example oil-seed rape.

There are clearly two ACCase genes in maize. As only one band is observed when a northern blot of maize leaf RNA is hybridised with the A3 cDNA it would seem the messenger RNAs for both genes are the same size. More A3-like than A4-like clones were selected from the maize leaf cDNA library so the A3 mRNA must be the more abundant. Of the three cDNA clones initially selected from the maize expression library by their reaction with antibodies to maize ACCase, A1 and A3 gave the strongest signal with the antibody and A4 the weakest. This could indicate that the A3-like cDNAs encode the grass-weed herbicide-sensitive form of ACCase. Whether the enzyme encoded by the A4-like cDNA is herbicide-sensitive or tolerant is unclear.

By defining the 5' end of a full-length maize cDNA it will be possible to isolate the promoter sequence from a maize genomic clone. Similarly it will be possible to isolate the promoter for the Arabidopsis gene and by reciprocal constructions to express the herbicide-tolerant Arabidopsis enzyme in herbicide-sensitive monocot species (for example, maize, wheat, barley, rice). This provides a method for producing monocotyledonous crop plants tolerant to herbicides (such as fluazifop) that are active by interfering with the fatty acid biosynthesis pathway.

Finally, the invention enables the use of a full-length cDNA clone to synthesise active ACCase in a transformed micro-organism culture, such as an *E. coli* or yeast system. Such a system would be useful for selecting herbicide-resistant forms of the ACCase enzyme, and for testing new compounds for herbicidal activity. It would also allow investigation of the nature of the herbicide-binding site and of the basis of at least one of the mechanisms responsible for resistance to grass-weed herbicides.

Note: FIG. 2 shows restriction digests of the A4-like (ACC12) and the A3-like (ACC34) maize ACCase cDNA clones. The oddnumbered lanes show ACC12 and the even-numbered ones show ACC34. The enzymes used are Pst1 (1,2), BamH1+Bg1III (3,4), HindIII (5,6), HincII (7,8), EcoR1 (9,10), AccI (11,12), PvuII (13,14), PvuII+HincII (15,16), PvuII+EcoRV (17,18). Marker lanes (M) are λ DNA digested with HindIII.

---

We claim:

1. An isolated DNA sequence selected from the group consisting of that depicted in any one of FIGS. 3 (SEQ ID NO:1), 4(a) (SEQ ID NO:3); 4(b) (SEQ ID NO:5), 5(a) (SEQ ID NO:7), 5(b) (SEQ ID NO:9), and 5(c) (SEQ ID NO:11), wherein said sequence encodes a plant acetyl CoA carboxylase or portion thereof.

2. The DNA sequence according to claim 1, flanked by heterologous DNA.

3. The DNA sequence according to claim 2, wherein the heterologous DNA comprises a plant operable promoter.

4. A clone selected from the group consisting of clones A3 and A4 which are deposited at the Australian Government Analytical Laboratory under the designations maize A3 ACC cDNA plasmid (Accession No. N91/074874) and maize A4 ACC cDNA plasmid (Accession No. N91/074875), respectively.

5. A clone encoding a plant acetyl CoA carboxylase, said clone having been obtained by probing plant genomic or cDNA libraries, using as probe a DNA sequence of claim 1.

6. A plant which has been transformed with the DNA sequence of claim 3, or the clone of claim 5.

\* \* \* \* \*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
  ( A ) LENGTH: 4345 base pairs
  ( B ) TYPE: nucleic acid
  ( C ) STRANDEDNESS: both
  ( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| GTTTTTTTTT | TTTTATTTCA | TGGCAGTCTG | ACGTGATTGA | AACATTGCGG | CATCAGCACA | 60 |
| GTAAAGACCT | GCAGAAGGTT | GTAGACATTG | TGTTGTCTCA | CCAGGGTGTG | AGGAACAAAG | 120 |
| CTAAGCTTGT | AACGGCACTT | ATGGAAAAGC | TGGTTTATCC | AAATCCTGGT | GGTTACAGGG | 180 |
| ATCTGTTAGT | TCGCTTTTCT | TCCCTCAATC | ATAAAGATA | TTATAAGTTG | GCCCTTAAAG | 240 |
| CAAGTGAACT | TCTTGAACAA | ACCAAACTAA | GTGAACTCCG | TGCAAGCGTT | GCAAGAAGCC | 300 |
| TTTCGGATCT | GGGGATGCAT | AAGGGAGAAA | TGAGTATTAA | GGATAACATG | GAAGATTTAG | 360 |
| TCTCTGCCCC | ATTACCTGTT | GAAGATGCTC | TGATTTCTTT | GTTGATTAC | AGTGATCGAA | 420 |
| CTGTTCAGCA | GAAAGTGATT | GAGACATACA | TATCACGATT | GTACCAGCCT | CATCTTGTAA | 480 |
| AGGATAGCAT | CCAAATGAAA | TTCAAGGAAT | CTGGTGCTAT | TACTTTTTGG | GAATTTTATG | 540 |
| AAGGGCATGT | TGATACTAGA | AATGGACATG | GGCTATTAT | TGGTGGGAAG | CGATGGGGTG | 600 |
| CCATGGTCGT | TCTCAAATCA | CTTGAATCTG | CGTCAACAGC | CATTGTGGCT | GCATTAAAGG | 660 |
| ATTCGGCACA | GTTCAACAGC | TCTGAGGGCA | ACATGATGCA | CATTGCATTA | TTGAGTGCTG | 720 |
| AAAATGAAAG | TAATATAAGT | GGAATAAGTG | ATGATCAAGC | TCAACATAAG | ATGGAAAAGC | 780 |
| TTAGCAAGAT | ACTGAAGGAT | ACTAGCGTTG | CAAGTGATCT | CCAAGCTGCT | GGTTTGAAGG | 840 |
| TTATAAGTTG | CATTGTTCAA | AGAGATGAAG | CTCGCATGCC | AATGCGCCAC | ACATTCCTCT | 900 |
| GGTTGGATGA | CAAGAGTTGT | TATGAAGAAG | AGCAGATTCT | CCGGCATGTG | GAGCCTCCCC | 960 |
| TCTCTACACT | TCTTGAATTG | GATAAGTTGA | AGGTGAAAGG | ATACAATGAA | ATGAAGTATA | 1020 |
| CTCCTTCGCG | TGACCGCCAA | TGGCATATCT | ACACACTAAG | AAATACTGAA | AACCCCAAAA | 1080 |
| TGTTGCATAG | GGTGTTTTC | CGAACTATTG | TCAGGCAACC | CAATGCAGGC | AACAAGTTTA | 1140 |
| CATCGGCTCA | GATCAGCGAC | GCTGAAGTAG | GATGTCCCGA | AGAATCTCTT | TCATTTACAT | 1200 |
| CAAATAGCAT | CTTAAGATCA | TTGATGACTG | CTATTGAAGA | ATTAGAGCTT | CATGCAATTA | 1260 |
| GGACAGGTCA | TTCTCACATG | TATTTGTGCA | TACTGAAAGA | GCAAAAGCTT | CTTGACCTCA | 1320 |
| TTCCATTTTC | AGGGAGTACA | ATTGTTGATG | TTGGCCAAGA | TGAAGCTACC | GCTTGTTCAC | 1380 |
| TTTTAAAATC | AATGGCTTTG | AAGATACATG | AGCTTGTTGG | TGCAAGGATG | CATCATCTGT | 1440 |
| CTGTATGCCA | GTGGGAGGTG | AAACTCAAGT | TGGACTGTGA | TGGCCCTGCA | AGTGGTACCT | 1500 |
| GGAGAGTTGT | AACTACAAAT | GTTACTGGTC | ACACCTGCAC | CATTGATATA | TACCGAGAAG | 1560 |
| TGGAGGAAAT | AGAATCGCAG | AAGTTAGTGG | TACCATTCAG | CCACTTCGTC | AGCTGGACCA | 1620 |
| TTGCATGGTG | TGCACTGAAT | AATCCATATC | AACCTTTGAG | TGTGATTGAT | CTAAAGCGCT | 1680 |
| GCTCTGCTAG | GAACAACAGA | ACAACATATT | GCTATGATTT | TCCGCTGGCC | TTTGAAACTG | 1740 |
| CACTGCAGAA | GTCATGGCAG | TCCAATGGCT | CTACTGTTTC | TGAAGGCAAT | GAAAATAGTA | 1800 |
| AATCCTACGT | GAAGGCAACT | GAGCTAGTGT | TTGCTGAAAA | ACATGGGTCC | TGGGGCACTC | 1860 |
| CTATAATTCC | GATGGAACCG | CTGCTGGGCT | CAACGACATT | GGTATGGTCG | CTTGGATCAT | 1920 |
| GGAGATGTCA | ACACCTGAAT | TTCCCAATGG | CAGGCAGATT | ATTGTTGTAG | CAAATGATAT | 1980 |
| CACTTTCAGA | GCTGGATCAT | TTGGCCCAAG | GGAAGATGCA | TTTTTTGAAA | CTGTCACTAA | 2040 |
| CCTGGCTTGC | GAAAGGAAAC | TTCCTCTTAT | ATACTTGGCA | GCAAACTCTG | GTTCTAGGAT | 2100 |

| | | | | | |
|---|---|---|---|---|---|
| TGGCATAGCT | GATGAAGTAA | AATCTTGCTT | CCGTGTTGGA | TGGTCTGACG | AAGGCAGTCC | 2160
| TGAACGAGGG | TTTCAGTACA | TCTATCTGAC | TGAAGAAGAC | TATGCTCGCA | TTAGCTCTTC | 2220
| TGTTATAGCA | CATAAGCTGG | AGCTAGATAG | TGGTGAAATT | AGGTGGATTA | TTGACTCTGT | 2280
| TGTGGGCAAG | GAGGATGGGC | TTGGTGTCGA | GAACATACAT | GGAAGTGCTG | CTATTGCCAG | 2340
| TGCTTATTCT | AGGGCATATG | AGGAGACATT | TACACTTACA | TTTGTGACTG | GGCGGACTGT | 2400
| AGGAATAGGA | GCTTATCTTG | CTCGACTTGG | TATACGGTGC | ATACAGCGTC | TTGACCAGCC | 2460
| TATTATTTTA | ACAGGGTTTT | CTGCCCTGAA | CAAGCTCCTT | GGGCGGGAAG | TGTACAGCTC | 2520
| CCACATGCAG | CTTGGTGGTC | CTAAGATCAT | GGCGACCAAT | GGTGTTGTCC | ACCTCACTGT | 2580
| TCCAGATGAC | CTTGAAGGTG | TTTCCAATAT | ATTGAGGTGG | CTCAGCTATG | TTCCTGCAAA | 2640
| CATTGGTGGA | CCTCTTCCTA | TTACCAAACC | TCTGGACCCT | CCAGACAGAC | CTGTTGCTTA | 2700
| CATCCCTGAG | AACACATGCG | ATCCACGTGC | AGCTATCTGT | GGTGTAGATG | ACAGCCAAGG | 2760
| GAAATGGTTG | GGTGGTATGT | TTGACAAAGA | CAGCTTTGTG | GAGACATTTG | AAGGATGGGC | 2820
| AAAAACAGTG | GTTACTGGCA | GAGCAAAGCT | TGGAGGAATT | CCTGTGGGCG | TCATAGCTGT | 2880
| GGAGACACAG | ACCATGATGC | AGATCATCCC | TGCTGATCCA | GGTCAGCTTG | ATTCCCATGA | 2940
| GCGATCTGTC | CCTCGTGCTG | GACAAGTGTG | GTTCCCAGAT | TCTGCAACCA | AGACCGCTCA | 3000
| GGCATTATTA | GACTTCAACC | GTGAAGGATT | GCCTCTGTTC | ATCCTGGCTA | ATTGGAGAGG | 3060
| CTTCTCTGGT | GGACAAAGAG | ATCTCTTTGA | AGGAATTCTT | CAGGCTGGGT | CAACAATTGT | 3120
| CGAGAACCTT | AGGACATATA | ATCAGCCTGC | TTTTGTGTAC | ATTCCTATGG | CTGGAGAGCT | 3180
| TCGTGGAGGA | GCTTGGGTTG | TGGTCGATAG | CAAAATAAAT | CCAGACCGCA | TTGAGTGTTA | 3240
| TGCTGAAAGG | ACTGCCAAAG | GTAATGTTCT | CGAACCTCAA | GGGTTAATTG | AAATCAAGTT | 3300
| CAGGTCAGAG | GAACTCCAAG | ACTGTATGGG | TAGGCTTGAC | CCAGAGTTGA | TAAATCTGAA | 3360
| AGCAAAACTC | CAAGATGTAA | ATCATGGAAA | TGGAAGTCTA | CCAGACATAG | AAGGGATTCG | 3420
| GAAGAGTATA | GAAGCACGTA | CGAAACAGTT | GCTGCCTTTA | TATACCCAGA | TTGCAATACG | 3480
| GTTTGCTGAA | TTGCATGATA | CTTCCCTAAG | AATGGCAGCT | AAAGGTGTGA | TTAAGAAAGT | 3540
| TGTAGACTGG | GAAGAATCAC | GCTCGTTCTT | CTATAAAAGG | CTACGGAGGA | GGATCGCAGA | 3600
| AGATGTTCTT | GCAAAAGAAA | TAAGGCAGAT | AGTCGGTGAT | AAATTTACGC | ACCAATTAGC | 3660
| AATGGAGCTC | ATCAAGGAAT | GGTACCTTGC | TTCTCAGGCC | ACAACAGGAA | GCACTGGATG | 3720
| GGATGACGAT | GATGCTTTTG | TTGCCTGGAA | GGACAGTCCT | GAAAACTACA | AGGGGCATAT | 3780
| CCAAAAGCTT | AGGGCTCAAA | AAGTGTCTCA | TTCGCTCTCT | GATCTTGCTG | ACTCCAGTTC | 3840
| AGATCTGCAA | GCATTCTCGC | AGGGTCTTTC | TACGCTATTA | GATAAGATGG | ATCCCTCTCA | 3900
| GAGAGCGAAG | TTTGTTCAGG | AAGTCAAGAA | GGTCCTTGAT | TGATGATACC | AACACATCCA | 3960
| ACACAATGTG | TGCATGTCAC | ATCTTTTGT | TCTAGTACAT | ACATAGAAGG | ATATTGCTTG | 4020
| GTCTTGATTG | ATCATGTCTG | ATTTAAGTCG | ACTATTATTT | CTTGGAATTT | TCTTTTGGAC | 4080
| CTGGTGCTAT | GGTTGATGGA | TGTATATTGG | ATATGTGCGT | TCTGCCAGGT | GTAAGCACAA | 4140
| AGGTTTAGAC | AGACCGAGAG | CAAGAGCGAG | TGAACCTGTT | CTGGTTTTGC | AGTGGTTCAG | 4200
| TAAGGCAGAA | AGTTGTTAAA | CCGTAGTTCT | GAGATGTATT | ACCAGTGGCG | CCATGCTGTA | 4260
| CTTTTAGGGT | GTATAATGCG | GATACAAATA | AACAATTTAG | CGGTTCATTA | AAGTTTGAAC | 4320
| TCAAATAAAA | AAAAAAAAAA | AAAAA | | | | 4345

( 2 ) INFORMATION FOR SEQ ID NO:2:

( i ) SEQUENCE CHARACTERISTICS:

(A) LENGTH: 1313 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:2:

| Phe | Phe | Phe | Phe | Ile | Ser | Trp | Gln | Ser | Asp | Val | Ile | Glu | Thr | Leu | Arg |
| 1 | | | | 5 | | | | | 10 | | | | | 15 | |

| His | Gln | His | Ser | Lys | Asp | Leu | Gln | Lys | Val | Val | Asp | Ile | Val | Leu | Ser |
| | | | 20 | | | | 25 | | | | | 30 | | | |

| His | Gln | Gly | Val | Arg | Asn | Lys | Ala | Lys | Leu | Val | Thr | Ala | Leu | Met | Glu |
| | | 35 | | | | | 40 | | | | | 45 | | | |

| Lys | Leu | Val | Tyr | Pro | Asn | Pro | Gly | Gly | Tyr | Arg | Asp | Leu | Leu | Val | Arg |
| | 50 | | | | | 55 | | | | | 60 | | | | |

| Phe | Ser | Ser | Leu | Asn | His | Lys | Arg | Tyr | Tyr | Lys | Leu | Ala | Leu | Lys | Ala |
| 65 | | | | | 70 | | | | | 75 | | | | | 80 |

| Ser | Glu | Leu | Leu | Glu | Gln | Thr | Lys | Leu | Ser | Glu | Leu | Arg | Ala | Ser | Val |
| | | | | 85 | | | | | 90 | | | | | 95 | |

| Ala | Arg | Ser | Leu | Ser | Asp | Leu | Gly | Met | His | Lys | Gly | Glu | Met | Ser | Ile |
| | | | 100 | | | | | 105 | | | | | 110 | | |

| Lys | Asp | Asn | Met | Glu | Asp | Leu | Val | Ser | Ala | Pro | Leu | Pro | Val | Glu | Asp |
| | | 115 | | | | | 120 | | | | | 125 | | | |

| Ala | Leu | Ile | Ser | Leu | Phe | Asp | Tyr | Ser | Asp | Arg | Thr | Val | Gln | Gln | Lys |
| | 130 | | | | | 135 | | | | | 140 | | | | |

| Val | Ile | Glu | Thr | Tyr | Ile | Ser | Arg | Leu | Tyr | Gln | Pro | His | Leu | Val | Lys |
| 145 | | | | | 150 | | | | | 155 | | | | | 160 |

| Asp | Ser | Ile | Gln | Met | Lys | Phe | Lys | Glu | Ser | Gly | Ala | Ile | Thr | Phe | Trp |
| | | | | 165 | | | | | 170 | | | | | 175 | |

| Glu | Phe | Tyr | Glu | Gly | His | Val | Asp | Thr | Arg | Asn | Gly | His | Gly | Ala | Ile |
| | | | 180 | | | | | 185 | | | | | 190 | | |

| Ile | Gly | Gly | Lys | Arg | Trp | Gly | Ala | Met | Val | Val | Leu | Lys | Ser | Leu | Glu |
| | | 195 | | | | | 200 | | | | | 205 | | | |

| Ser | Ala | Ser | Thr | Ala | Ile | Val | Ala | Ala | Leu | Lys | Asp | Ser | Ala | Gln | Phe |
| | 210 | | | | | 215 | | | | | 220 | | | | |

| Asn | Ser | Ser | Glu | Gly | Asn | Met | Met | His | Ile | Ala | Leu | Leu | Ser | Ala | Glu |
| 225 | | | | | 230 | | | | | 235 | | | | | 240 |

| Asn | Glu | Ser | Asn | Ile | Ser | Gly | Ile | Ser | Asp | Asp | Gln | Ala | Gln | His | Lys |
| | | | | 245 | | | | | 250 | | | | | 255 | |

| Met | Glu | Lys | Leu | Ser | Lys | Ile | Leu | Lys | Asp | Thr | Ser | Val | Ala | Ser | Asp |
| | | | 260 | | | | | 265 | | | | | 270 | | |

| Leu | Gln | Ala | Ala | Gly | Leu | Lys | Val | Ile | Ser | Cys | Ile | Val | Gln | Arg | Asp |
| | 275 | | | | | 280 | | | | | 285 | | | | |

| Glu | Ala | Arg | Met | Pro | Met | Arg | His | Thr | Phe | Leu | Trp | Leu | Asp | Asp | Lys |
| 290 | | | | | 295 | | | | | 300 | | | | | |

| Ser | Cys | Tyr | Glu | Glu | Glu | Gln | Ile | Leu | Arg | His | Val | Glu | Pro | Pro | Leu |
| 305 | | | | | 310 | | | | | 315 | | | | | 320 |

| Ser | Thr | Leu | Leu | Glu | Leu | Asp | Lys | Leu | Lys | Val | Lys | Gly | Tyr | Asn | Glu |
| | | | | 325 | | | | | 330 | | | | | 335 | |

| Met | Lys | Tyr | Thr | Pro | Ser | Arg | Asp | Arg | Gln | Trp | His | Ile | Tyr | Thr | Leu |
| | | | 340 | | | | | 345 | | | | | 350 | | |

| Arg | Asn | Thr | Glu | Asn | Pro | Lys | Met | Leu | His | Arg | Val | Phe | Phe | Arg | Thr |
| | | 355 | | | | | 360 | | | | | 365 | | | |

| Ile | Val | Arg | Gln | Pro | Asn | Ala | Gly | Asn | Lys | Phe | Thr | Ser | Ala | Gln | Ile |
| | 370 | | | | | 375 | | | | | 380 | | | | |

-continued

```
Ser  Asp  Ala  Glu  Val  Gly  Cys  Pro  Glu  Glu  Ser  Leu  Ser  Phe  Thr  Ser
385                 390                 395                           400

Asn  Ser  Ile  Leu  Arg  Ser  Leu  Met  Thr  Ala  Ile  Glu  Glu  Leu  Glu  Leu
                    405                 410                      415

His  Ala  Ile  Arg  Thr  Gly  His  Ser  His  Met  Tyr  Leu  Cys  Ile  Leu  Lys
                    420                 425                      430

Glu  Gln  Lys  Leu  Leu  Asp  Leu  Ile  Pro  Phe  Ser  Gly  Ser  Thr  Ile  Val
          435                 440                      445

Asp  Val  Gly  Gln  Asp  Glu  Ala  Thr  Ala  Cys  Ser  Leu  Leu  Lys  Ser  Met
     450                      455                      460

Ala  Leu  Lys  Ile  His  Glu  Leu  Val  Gly  Ala  Arg  Met  His  His  Leu  Ser
465                 470                      475                           480

Val  Cys  Gln  Trp  Glu  Val  Lys  Leu  Lys  Leu  Asp  Cys  Asp  Gly  Pro  Ala
                    485                 490                      495

Ser  Gly  Thr  Trp  Arg  Val  Val  Thr  Thr  Asn  Val  Thr  Gly  His  Thr  Cys
               500                 505                      510

Thr  Ile  Asp  Ile  Tyr  Arg  Glu  Val  Glu  Glu  Ile  Glu  Ser  Gln  Lys  Leu
          515                 520                      525

Val  Val  Pro  Phe  Ser  His  Phe  Val  Ser  Trp  Thr  Ile  Ala  Trp  Cys  Ala
     530                 535                      540

Leu  Asn  Asn  Pro  Tyr  Gln  Pro  Leu  Ser  Val  Ile  Asp  Leu  Lys  Arg  Cys
545                 550                      555                           560

Ser  Ala  Arg  Asn  Asn  Arg  Thr  Thr  Tyr  Cys  Tyr  Asp  Phe  Pro  Leu  Ala
                    565                      570                      575

Phe  Glu  Thr  Ala  Leu  Gln  Lys  Ser  Trp  Gln  Ser  Asn  Gly  Ser  Thr  Val
               580                      585                      590

Ser  Glu  Gly  Asn  Glu  Asn  Ser  Lys  Ser  Tyr  Val  Lys  Ala  Thr  Glu  Leu
               595                      600                      605

Val  Phe  Ala  Glu  Lys  His  Gly  Ser  Trp  Gly  Thr  Pro  Ile  Ile  Pro  Met
     610                      615                      620

Xaa  Thr  Ala  Ala  Gly  Leu  Asn  Asp  Ile  Gly  Met  Val  Ala  Trp  Ile  Met
625                      630                      635                      640

Glu  Met  Ser  Thr  Pro  Glu  Phe  Pro  Asn  Gly  Arg  Gln  Ile  Ile  Val  Val
               645                      650                           655

Ala  Asn  Asp  Ile  Thr  Phe  Arg  Ala  Gly  Ser  Phe  Gly  Pro  Arg  Glu  Asp
               660                      665                      670

Ala  Phe  Phe  Glu  Thr  Val  Thr  Asn  Leu  Ala  Cys  Glu  Arg  Lys  Leu  Pro
          675                      680                      685

Leu  Ile  Tyr  Leu  Ala  Ala  Asn  Ser  Gly  Ser  Arg  Ile  Gly  Ile  Ala  Asp
     690                      695                      700

Glu  Val  Lys  Ser  Cys  Phe  Arg  Val  Gly  Trp  Ser  Asp  Glu  Gly  Ser  Pro
705                 710                      715                           720

Glu  Arg  Gly  Phe  Gln  Tyr  Ile  Tyr  Leu  Thr  Glu  Glu  Asp  Tyr  Ala  Arg
                    725                      730                      735

Ile  Ser  Ser  Ser  Val  Ile  Ala  His  Lys  Leu  Glu  Leu  Asp  Ser  Gly  Glu
               740                      745                      750

Ile  Arg  Trp  Ile  Ile  Asp  Ser  Val  Val  Gly  Lys  Glu  Asp  Gly  Leu  Gly
          755                      760                      765

Val  Glu  Asn  Ile  His  Gly  Ser  Ala  Ala  Ile  Ala  Ser  Ala  Tyr  Ser  Arg
     770                      775                      780

Ala  Tyr  Glu  Glu  Thr  Phe  Thr  Leu  Thr  Phe  Val  Thr  Gly  Arg  Thr  Val
785                      790                      795                      800

Gly  Ile  Gly  Ala  Tyr  Leu  Ala  Arg  Leu  Gly  Ile  Arg  Cys  Ile  Gln  Arg
```

-continued

```
                    805                           810                           815
Leu  Asp  Gln  Pro  Ile  Ile  Leu  Thr  Gly  Phe  Ser  Ala  Leu  Asn  Lys  Leu
               820                      825                      830

Leu  Gly  Arg  Glu  Val  Tyr  Ser  Ser  His  Met  Gln  Leu  Gly  Gly  Pro  Lys
               835                      840                      845

Ile  Met  Ala  Thr  Asn  Gly  Val  Val  His  Leu  Thr  Val  Pro  Asp  Asp  Leu
850                           855                           860

Glu  Gly  Val  Ser  Asn  Ile  Leu  Arg  Trp  Leu  Ser  Tyr  Val  Pro  Ala  Asn
865                      870                      875                      880

Ile  Gly  Gly  Pro  Leu  Pro  Ile  Thr  Lys  Pro  Leu  Asp  Pro  Pro  Asp  Arg
                    885                      890                      895

Pro  Val  Ala  Tyr  Ile  Pro  Glu  Asn  Thr  Cys  Asp  Pro  Arg  Ala  Ala  Ile
                    900                      905                      910

Cys  Gly  Val  Asp  Asp  Ser  Gln  Gly  Lys  Trp  Leu  Gly  Gly  Met  Phe  Asp
               915                      920                      925

Lys  Asp  Ser  Phe  Val  Glu  Thr  Phe  Glu  Gly  Trp  Ala  Lys  Thr  Val  Val
               930                      935                      940

Thr  Gly  Arg  Ala  Lys  Leu  Gly  Gly  Ile  Pro  Val  Gly  Val  Ile  Ala  Val
945                      950                      955                           960

Glu  Thr  Gln  Thr  Met  Met  Gln  Ile  Ile  Pro  Ala  Asp  Pro  Gly  Gln  Leu
                    965                      970                      975

Asp  Ser  His  Glu  Arg  Ser  Val  Pro  Arg  Ala  Gly  Gln  Val  Trp  Phe  Pro
               980                      985                      990

Asp  Ser  Ala  Thr  Lys  Thr  Ala  Gln  Ala  Leu  Leu  Asp  Phe  Asn  Arg  Glu
               995                      1000                     1005

Gly  Leu  Pro  Leu  Phe  Ile  Leu  Ala  Asn  Trp  Arg  Gly  Phe  Ser  Gly  Gly
1010                     1015                     1020

Gln  Arg  Asp  Leu  Phe  Glu  Gly  Ile  Leu  Gln  Ala  Gly  Ser  Thr  Ile  Val
1025                     1030                     1035                     1040

Glu  Asn  Leu  Arg  Thr  Tyr  Asn  Gln  Pro  Ala  Phe  Val  Tyr  Ile  Pro  Met
                    1045                     1050                     1055

Ala  Gly  Glu  Leu  Arg  Gly  Gly  Ala  Trp  Val  Val  Val  Asp  Ser  Lys  Ile
                    1060                     1065                     1070

Asn  Pro  Asp  Arg  Ile  Glu  Cys  Tyr  Ala  Glu  Arg  Thr  Ala  Lys  Gly  Asn
               1075                     1080                     1085

Val  Leu  Glu  Pro  Gln  Gly  Leu  Ile  Glu  Ile  Lys  Phe  Arg  Ser  Glu  Glu
               1090                     1095                     1100

Leu  Gln  Asp  Cys  Met  Gly  Arg  Leu  Asp  Pro  Glu  Leu  Ile  Asn  Leu  Lys
1105                     1110                     1115                     1120

Ala  Lys  Leu  Gln  Asp  Val  Asn  His  Gly  Asn  Gly  Ser  Leu  Pro  Asp  Ile
                    1125                     1130                     1135

Glu  Gly  Ile  Arg  Lys  Ser  Ile  Glu  Ala  Arg  Thr  Lys  Gln  Leu  Leu  Pro
                    1140                     1145                     1150

Leu  Tyr  Thr  Gln  Ile  Ala  Ile  Arg  Phe  Ala  Glu  Leu  His  Asp  Thr  Ser
               1155                     1160                     1165

Leu  Arg  Met  Ala  Ala  Lys  Gly  Val  Ile  Lys  Lys  Val  Val  Asp  Trp  Glu
               1170                     1175                     1180

Glu  Ser  Arg  Ser  Phe  Phe  Tyr  Lys  Arg  Leu  Arg  Arg  Arg  Ile  Ala  Glu
1185                     1190                     1195                     1200

Asp  Val  Leu  Ala  Lys  Glu  Ile  Arg  Gln  Ile  Val  Gly  Asp  Lys  Phe  Thr
                    1205                     1210                     1215

His  Gln  Leu  Ala  Met  Glu  Leu  Ile  Lys  Glu  Trp  Tyr  Leu  Ala  Ser  Gln
                    1220                     1225                     1230
```

| | | | | | | | | | | | | | | |
|---|---|---|---|---|---|---|---|---|---|---|---|---|---|---|
|Ala|Thr|Thr|Gly|Ser|Thr|Gly|Trp|Asp|Asp|Asp|Ala|Phe|Val|Ala|
| |1235| | | | | |1240| | | |1245| | | |

| | | | | | | | | | | | | | | |
|---|---|---|---|---|---|---|---|---|---|---|---|---|---|---|
|Trp|Lys|Asp|Ser|Pro|Glu|Asn|Tyr|Lys|Gly|His|Ile|Gln|Lys|Leu|Arg|
| |1250| | | | |1255| | | |1260| | | | |

| | | | | | | | | | | | | | | |
|---|---|---|---|---|---|---|---|---|---|---|---|---|---|---|
|Ala|Gln|Lys|Val|Ser|His|Ser|Leu|Ser|Asp|Leu|Ala|Asp|Ser|Ser|Ser|
|1265| | | | |1270| | | |1275| | | | |1280|

| | | | | | | | | | | | | | | |
|---|---|---|---|---|---|---|---|---|---|---|---|---|---|---|
|Asp|Leu|Gln|Ala|Phe|Ser|Gln|Gly|Leu|Ser|Thr|Leu|Leu|Asp|Lys|Met|
| | | | |1285| | | | |1290| | | | |1295|

| | | | | | | | | | | | | | | |
|---|---|---|---|---|---|---|---|---|---|---|---|---|---|---|
|Asp|Pro|Ser|Gln|Arg|Ala|Lys|Phe|Val|Gln|Glu|Val|Lys|Lys|Val|Leu|
| | | |1300| | | | |1305| | | |1310| | |

Asp (2) INFORMATION FOR SEQ ID NO:3:

(i) SEQUENCE CHARACTERISTICS:
(A) LENGTH: 400 base pairs
(B) TYPE: nucleic acid
(C) STRANDEDNESS: both
(D) TOPOLOGY: linear (ii) MOLECULE TYPE: DNA (genomic)

(xi) SEQUENCE DESCRIPTION: SEQ ID NO:3:

| | | | | | | |
|---|---|---|---|---|---|---|
|CAAATACACA|ATTGAATCTG|TAAGGACTGG|ACATGGTAGC|TACAGGTTGA|GAGTGAATGA|60|
|TTCAACAGTT|GAAGCGAATG|TACAATCTTT|ATGTGATGGT|GGCCTCTTAA|TGCAGTTGGA|120|
|TGGAAACAGC|CATGTAATTT|ATGCAGAAGA|AGAAGCTGGT|GGTACACGGC|TTCAGATTGA|180|
|TGGAAAGACA|TGTTTATTGC|AGAATGACCA|TGATCCATCA|AAGTTATTAG|CTGAGACACC|240|
|CTGCAAACTT|CTTCGTTTCT|TGGTTGCTGA|TGGTGCTCAT|GTTGATGCGG|ATGTACCATA|300|
|CGCGGAAGTT|GAGGTTATGA|AGATGTGCAT|GCCTCTCTTG|TCACCTGCTT|CTGGTGTCAT|360|
|TCATTGTATG|ATGTCTGAGG|GCCAGGCATT|GCAGGCTGGT| | |400|

(2) INFORMATION FOR SEQ ID NO:4:

(i) SEQUENCE CHARACTERISTICS:
(A) LENGTH: 133 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:4:

| | | | | | | | | | | | | | | |
|---|---|---|---|---|---|---|---|---|---|---|---|---|---|---|
|Lys|Tyr|Thr|Ile|Glu|Ser|Val|Arg|Thr|Gly|His|Gly|Ser|Tyr|Arg|Leu|
|1| | | |5| | | | |10| | | | |15| |

| | | | | | | | | | | | | | | |
|---|---|---|---|---|---|---|---|---|---|---|---|---|---|---|
|Arg|Val|Asn|Asp|Ser|Thr|Val|Glu|Ala|Asn|Val|Gln|Ser|Leu|Cys|Asp|
| | | |20| | | | |25| | | | |30| | |

| | | | | | | | | | | | | | | |
|---|---|---|---|---|---|---|---|---|---|---|---|---|---|---|
|Gly|Gly|Leu|Leu|Met|Gln|Leu|Asp|Gly|Asn|Ser|His|Val|Ile|Tyr|Ala|
| | | | |35| | | | |40| | | | |45| |

| | | | | | | | | | | | | | | |
|---|---|---|---|---|---|---|---|---|---|---|---|---|---|---|
|Glu|Glu|Glu|Ala|Gly|Gly|Thr|Arg|Leu|Gln|Ile|Asp|Gly|Lys|Thr|Cys|
| | | |50| | | | |55| | | | |60| | |

| | | | | | | | | | | | | | | |
|---|---|---|---|---|---|---|---|---|---|---|---|---|---|---|
|Leu|Leu|Gln|Asn|Asp|His|Asp|Pro|Ser|Lys|Leu|Leu|Ala|Glu|Thr|Pro|
|65| | | | |70| | | | |75| | | | |80|

| | | | | | | | | | | | | | | |
|---|---|---|---|---|---|---|---|---|---|---|---|---|---|---|
|Cys|Lys|Leu|Leu|Arg|Phe|Leu|Val|Ala|Asp|Gly|Ala|His|Val|Asp|Ala|
| | | | |85| | | | |90| | | | |95| |

| | | | | | | | | | | | | | | |
|---|---|---|---|---|---|---|---|---|---|---|---|---|---|---|
|Asp|Val|Pro|Tyr|Ala|Glu|Val|Glu|Val|Met|Lys|Met|Cys|Met|Pro|Leu|
| | | |100| | | | |105| | | | |110| | |

| | | | | | | | | | | | | | | |
|---|---|---|---|---|---|---|---|---|---|---|---|---|---|---|
|Leu|Ser|Pro|Ala|Ser|Gly|Val|Ile|His|Cys|Met|Met|Ser|Glu|Gly|Gln|
| | | | |115| | | | |120| | | | |125| |

```
          Ala Leu Gln Ala Gly
              130
```

( 2 ) INFORMATION FOR SEQ ID NO:5:

( i ) SEQUENCE CHARACTERISTICS:
        ( A ) LENGTH: 230 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:5:

```
GTTGAATTTT  TACCATGGAA  AAAACGAGGA  CTTTCCATCC  AAGTTGCTAA  GAGACATCAT      60
TGAGGAAAAT  CTTTCTTATG  GTTCAGAGAA  GGAAAAGGCT  ACAAATGAGA  GGCTTGTTGA     120
GCCTCTTATG  AACCTACTGA  AGTCATATGA  GGGTGGGAGA  GAGAGCCATG  CACATTTTGT     180
TGTCAAGTCT  CTTTTCGAGG  AGTATCTTAC  AGTGGAAGAA  CTTTTTAGTG                 230
```

( 2 ) INFORMATION FOR SEQ ID NO:6:

( i ) SEQUENCE CHARACTERISTICS:
        ( A ) LENGTH: 76 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Leu Asn Phe Tyr His Gly Lys Asn Glu Asp Phe Pro Ser Lys Leu Leu
 1               5                  10                  15

Arg Asp Ile Ile Glu Glu Asn Leu Ser Tyr Gly Ser Glu Lys Glu Lys
                20                  25                  30

Ala Thr Asn Glu Arg Leu Val Glu Pro Leu Met Asn Leu Leu Lys Ser
            35                  40                  45

Tyr Glu Gly Gly Arg Glu Ser His Ala His Phe Val Val Lys Ser Leu
        50                  55                  60

Phe Glu Glu Tyr Leu Thr Val Glu Glu Leu Phe Ser
65                  70                  75
```

( 2 ) INFORMATION FOR SEQ ID NO:7:

( i ) SEQUENCE CHARACTERISTICS:
        ( A ) LENGTH: 250 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:7:

```
GTTCAAGCTG  AGAGGCCCCC  ATGGTATATC  TCAGTGGTTG  GAGGTGCTTT  ATATAAAACA      60
GTAACCACCA  ATGCAGCCAC  TGTTTCTGAA  TATGTTAGTT  ATCTCACCAA  AGGCCAGATT     120
CCACCAAAGC  ATATATCCCT  TGTCAATTCA  ACAGTTAATT  TGAATATAGA  AGGGAGCAAA     180
TACACAATTG  AAACTGTCAG  GACTGGGCAT  GGTAGGTACA  AGTTGCGAAT  GAATGATTCA     240
ACAGTTGAGG                                                                 250
```

( 2 ) INFORMATION FOR SEQ ID NO:8:

( i ) SEQUENCE CHARACTERISTICS:

(A) LENGTH: 83 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:8:

| Val | Gln | Ala | Glu | Arg | Pro | Pro | Trp | Tyr | Ile | Ser | Val | Val | Gly | Gly | Ala |
|---|---|---|---|---|---|---|---|---|---|---|---|---|---|---|---|
| 1 | | | | 5 | | | | | 10 | | | | | 15 | |

| Leu | Tyr | Lys | Thr | Val | Thr | Thr | Asn | Ala | Ala | Thr | Val | Ser | Glu | Tyr | Val |
|---|---|---|---|---|---|---|---|---|---|---|---|---|---|---|---|
| | | | 20 | | | | | 25 | | | | | 30 | | |

| Ser | Tyr | Leu | Thr | Lys | Gly | Gln | Ile | Pro | Pro | Lys | His | Ile | Ser | Leu | Val |
|---|---|---|---|---|---|---|---|---|---|---|---|---|---|---|---|
| | | | 35 | | | | 40 | | | | | 45 | | | |

| Asn | Ser | Thr | Val | Asn | Leu | Asn | Ile | Glu | Gly | Ser | Lys | Tyr | Thr | Ile | Glu |
|---|---|---|---|---|---|---|---|---|---|---|---|---|---|---|---|
| | 50 | | | | | 55 | | | | | 60 | | | | |

| Thr | Val | Arg | Thr | Gly | His | Gly | Arg | Tyr | Lys | Leu | Arg | Met | Asn | Asp | Ser |
|---|---|---|---|---|---|---|---|---|---|---|---|---|---|---|---|
| 65 | | | | | 70 | | | | | 75 | | | | | 80 |

| Thr | Val | Glu |
|---|---|---|

(2) INFORMATION FOR SEQ ID NO:9:

(i) SEQUENCE CHARACTERISTICS:
(A) LENGTH: 330 base pairs
(B) TYPE: nucleic acid
(C) STRANDEDNESS: both
(D) TOPOLOGY: linear (ii) MOLECULE TYPE: DNA (genomic)

(xi) SEQUENCE DESCRIPTION: SEQ ID NO:9:

```
TATGGTTCAG AGAAGGAAAA GGCTACAAAT GAGCGACTTG TTGAGCCTCT TATGAACCTA      60
CTGAAGTCAT ATGAGGGTGG GAGAGAAAGC CATGCACATT TTGTTGTCAA GTCTCTTTTT     120
GAGGAGTATC TTACCGTGGA AGAACTTTTC AGTGATGGCA TTCAGTCTGA CGTGATTGAA     180
ACCTTGCGTC ATCAGCACAG TAAAGACCTG CAGAAGGTTG TAGACATCGT GCTGTCTCAC     240
CAGGGTGTGA GGAACAAAGC TAAGCTTGTA ACAGCACTTA TGGAAAAGCT GGTTTATCCA     300
AATCCTGCAT TGCAAGAAGC CTTTCAGATC                                      330
```

(2) INFORMATION FOR SEQ ID NO:10:

(i) SEQUENCE CHARACTERISTICS:
(A) LENGTH: 110 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:10:

| Tyr | Gly | Ser | Glu | Lys | Glu | Lys | Ala | Thr | Asn | Glu | Arg | Leu | Val | Glu | Pro |
|---|---|---|---|---|---|---|---|---|---|---|---|---|---|---|---|
| 1 | | | | 5 | | | | | 10 | | | | | 15 | |

| Leu | Met | Asn | Leu | Leu | Lys | Ser | Tyr | Glu | Gly | Gly | Arg | Glu | Ser | His | Ala |
|---|---|---|---|---|---|---|---|---|---|---|---|---|---|---|---|
| | | | 20 | | | | | 25 | | | | | 30 | | |

| His | Phe | Val | Val | Lys | Ser | Leu | Phe | Glu | Glu | Tyr | Leu | Thr | Val | Glu | Glu |
|---|---|---|---|---|---|---|---|---|---|---|---|---|---|---|---|
| | | | 35 | | | | 40 | | | | | 45 | | | |

| Leu | Phe | Ser | Asp | Gly | Ile | Gln | Ser | Asp | Val | Ile | Glu | Thr | Leu | Arg | His |
|---|---|---|---|---|---|---|---|---|---|---|---|---|---|---|---|
| | 50 | | | | | 55 | | | | | 60 | | | | |

| Gln | His | Ser | Lys | Asp | Leu | Gln | Lys | Val | Val | Asp | Ile | Val | Leu | Ser | His |
|---|---|---|---|---|---|---|---|---|---|---|---|---|---|---|---|
| 65 | | | | | 70 | | | | | 75 | | | | | 80 |

| Gln | Gly | Val | Arg | Asn | Lys | Ala | Lys | Leu | Val | Thr | Ala | Leu | Met | Glu | Lys |
|---|---|---|---|---|---|---|---|---|---|---|---|---|---|---|---|

```
                                     85                              90                                 95
            Leu  Val  Tyr  Pro  Asn  Pro  Ala  Leu  Gln  Glu  Ala  Phe  Gln  Ile
                           100                 105                      110
```

( 2 ) INFORMATION FOR SEQ ID NO:11:

( i ) SEQUENCE CHARACTERISTICS:
        ( A ) LENGTH: 319 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:11:

```
TGCTTGCCCC  TTGATTGACC  ATGTCTGATC  CTAAGTCGAC  CATTATTTCC  TTGAAACTTC   60

CTTTCGGACG  TGGTGCTATG  GTTGATGAAT  TTGGATGTGT  GCGTTCTGCC  AGGTGTAAGC  120

CCAAAGGTTT  ATACAGACCG  AGTTAAGGTT  AGGAAGAGCA  CGAGTGAACC  TGTTCTGGTT  180

TTGCAGTGGT  TAAGGCAGAA  AGTTGTTTCA  CTGTAGTTCT  GAGATGTATT  ACCAGCGGCG  240

CTGTAATTTT  AGGGTGTATA  ATGCGGATGC  TAGTAAACAA  TTGAGTGGTT  CTTTAAAAAA  300

AAAAAAAAAA  AAAAAAAA                                                   319
```